(12) United States Patent
Murata et al.

(10) Patent No.: US 9,389,348 B1
(45) Date of Patent: Jul. 12, 2016

(54) COLOR MATERIAL, COLOR MATERIAL DISPERSION LIQUID, COLOR RESIN COMPOSITION FOR COLOR FILTERS, COLOR FILTER, LIQUID CRYSTAL DISPLAY DEVICE AND ORGANIC LIGHT-EMITTING DISPLAY DEVICE

(71) Applicant: DAI NIPPON PRINTING CO., LTD., Tokyo-to (JP)

(72) Inventors: Tomoki Murata, Tokyo-to (JP); Michihiro Ogura, Tokyo-to (JP); Masato Okada, Tokyo-to (JP); Daisuke Endo, Tokyo-to (JP); Fumiyasu Murakami, Tokyo-to (JP); Hiroaki Segawa, Tokyo-to (JP)

(73) Assignee: DAI NIPPON PRINTING CO., LTD., Tokyo-to (JP)

( * ) Notice: Subject to any disclaimer, the term of this patent is extended or adjusted under 35 U.S.C. 154(b) by 0 days.

(21) Appl. No.: 14/786,395

(22) PCT Filed: Mar. 28, 2014

(86) PCT No.: PCT/JP2014/059089
§ 371 (c)(1),
(2) Date: Jan. 4, 2016

(87) PCT Pub. No.: WO2014/174988
PCT Pub. Date: Oct. 30, 2014

(30) Foreign Application Priority Data

Apr. 26, 2013 (JP) ................................. 2013-094537
Oct. 23, 2013 (JP) ................................. 2013-220657

(51) Int. Cl.
| | | |
|---|---|---|
| G02B 5/20 | (2006.01) | |
| G02F 1/1335 | (2006.01) | |
| | G02B 5/22 | |
| (2006.01) | C07D 311/82 | |
| (2006.01) | C09B 69/06 | |
| (2006.01) | H01L 27/32 | |
| (2006.01) | G03F 7/00 | |
| (2006.01) | | |

(52) U.S. Cl.
CPC .............. *G02B 5/223* (2013.01); *C07D 311/82* (2013.01); *C09B 69/06* (2013.01); *G02F 1/133514* (2013.01); *H01L 27/322* (2013.01); *G03F 7/0007* (2013.01)

(58) Field of Classification Search
CPC . G03F 7/0007; G02B 5/223; G02F 1/133516; H01L 27/322; C09B 69/06; C07D 311/82
USPC ............................................. 430/7; 349/106
See application file for complete search history.

(56) References Cited

U.S. PATENT DOCUMENTS

| | | | |
|---|---|---|---|
| 2013/0018208 A1* | 1/2013 | Kondou et al. | ......... C09B 11/12 564/283 |
| 2014/0037866 A1 | 2/2014 | Okada | |
| 2014/0039201 A1 | 2/2014 | Okada et al. | |
| 2015/0368473 A1* | 12/2015 | Okada | ................. C09B 67/0084 257/40 |

FOREIGN PATENT DOCUMENTS

| | | |
|---|---|---|
| JP | 2010-237608 A | 10/2010 |
| JP | 2011-075661 A | 4/2011 |
| JP | 2012-233033 A | 11/2012 |
| JP | 2013-054200 A | 3/2013 |
| JP | 2013-076764 A | 4/2013 |
| WO | 2011/037195 A1 | 3/2011 |
| WO | 2011/108495 A1 | 9/2011 |
| WO | 2012/144520 A1 | 10/2012 |
| WO | 2012/144521 A1 | 10/2012 |
| WO | WO 2013/050431 A1 * | 4/2013 |

OTHER PUBLICATIONS

International Search Report mailed Jun. 10, 2014; PCT/JP2014/059089.

* cited by examiner

*Primary Examiner* — John A McPherson
(74) *Attorney, Agent, or Firm* — Ladas & Parry LLP

(57) ABSTRACT

The present invention is to provide a color material dispersion liquid which is able to form a high-luminance coating film having excellent heat resistance, with adjusting the color tone of the coating film to a desired color tone. Disclosed is a color material dispersion liquid containing: (A) a color material, (B) a dispersant and (C) a solvent, wherein the color material (A) contains a color material (A-1) in which at least a cation represented by the following general formula (I) and a monovalent anion represented by the following general formula (II) form a salt:

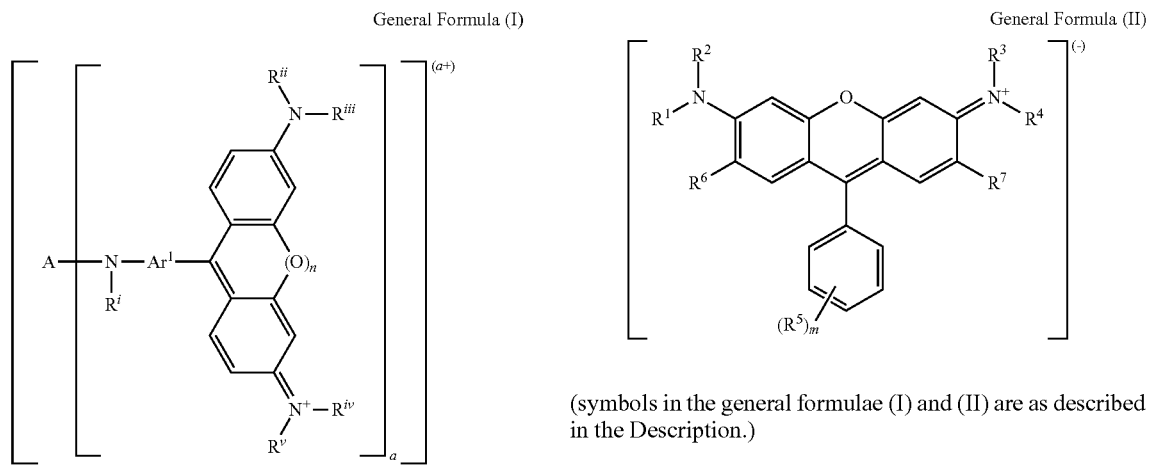
General Formula (I)
General Formula (II)
(symbols in the general formulae (I) and (II) are as described in the Description.)
10 Claims, 3 Drawing Sheets

COLOR MATERIAL, COLOR MATERIAL DISPERSION LIQUID, COLOR RESIN COMPOSITION FOR COLOR FILTERS, COLOR FILTER, LIQUID CRYSTAL DISPLAY DEVICE AND ORGANIC LIGHT-EMITTING DISPLAY DEVICE

TECHNICAL FIELD

The present invention relates to a color material, a color material dispersion liquid, a color resin composition for color filters, a color filter, a liquid crystal display device, and an organic light-emitting display device.

BACKGROUND ART

Many thin image display devices as typified by displays, i.e., flat panel displays, have been released on the market, because they are thinner than cathode-ray tube displays and they do not occupy much space in depth. Their market price has decreased year by year with advances in production techniques, resulting in a further increase in demand and a yearly increase in production. Especially, color LCD TVs have almost become the mainstream of TVs. Also in recent years, organic light-emitting display devices such as organic EL displays, which emit light by themselves and thereby have high visibility, have received attention as the next generation of image display devices. In relation to the performance of these image display devices, there is a strong demand for a further increase in image quality, such as an increase in contrast and color reproducibility, and a decrease in power consumption.

A color filter is used in these liquid crystal display devices and organic light-emitting display devices. For example, in the case of color LCDs, the amount of light is controlled by using a back light as the light source and electrically driving the liquid crystal. Colors are represented by the light that passed through the color filter. Accordingly, the color filter is indispensable for color representation in LCD TVs and plays a large role in determining display performance. In organic light-emitting display devices, a color image is formed in the same manner as liquid crystal display devices, when the color filter is used in combination with an organic, white light-emitting element.

A recent trend is that there is a demand for power-saving image display devices. To increase backlight use efficiency, there is a very high demand for high-luminance color filters. This is a major issue especially for mobile displays such as mobile phones, smart phones and tablet PCs.

Even though technological advances have increased battery capacity, there is still a limit on battery capacity of mobile devices. Meanwhile, there is a trend that power consumption has grown with the increase in screen size. Image display devices containing a color filter determine the design and performance of mobile terminal devices, because they are directly linked to the usable time and charging frequency of mobile terminal devices.

In general, a color filter has a transparent substrate, color layers made of color patterns of the three primary colors (red, green and blue), and a light shielding part formed on the transparent substrate so as to define each color pattern.

To form such color layers, a pigment dispersion method in which pigments with excellent heat resistance and light resistance are used as color materials, has been widely used. However, it is difficult for color filters produced by use of pigments to satisfy the latest demand for higher luminance.

As a means to achieve higher luminance, color resin compositions for color filters, which contain dyes, have been studied. Compared to pigments, dyes generally have a higher transmittance and are able to produce a high-luminance color filter. However, dyes are problematic in that they are inferior in heat resistance and light resistance to pigments and the chromaticity is likely to change when they are heated at high temperature in color filter production process, for example. Also, color resin compositions containing dyes have such a problem that aggregates are likely to be precipitated during drying process. Aggregates precipitated in a coating film lead to a remarkable deterioration in contrast and make it difficult to use the coating film as a color layer.

As a means to improve various kinds of resistance properties of dyes, a method for producing a salt-forming dye is known.

In Patent Literature 1, a color composition for color filters is disclosed as a color resin composition for color filters which is excellent in color characteristics, heat resistance, light resistance and solvent resistance, the color composition containing a salt-forming compound formed from a basic dye and an anion component having a molecular weight of 200 to 3,500. However, a color layer using the color composition for color filters disclosed in Patent Literature 1 shows insufficient heat resistance during a high-temperature heating step in a color filter production step.

In Patent Literature 2, a salt is disclosed as a dye with an excellent molar absorbance coefficient, the salt being formed from a cation having a xanthene skeleton and an anion having a triphenylmethane skeleton. In Patent Literature 2, the salt is described to be soluble in organic solvents, and it is not dispersed in resin compositions for use.

A color filter and so on are disclosed in Patent Literature 3 by the inventors of the present invention, which use specific color materials containing divalent or higher anions and divalent or higher cations, in which dye skeletons are crosslinked by crosslinking groups. It is disclosed that the color materials are excellent in heat resistance since, due to containing the divalent or higher anions, molecular associations are formed therein, and color filters using the color materials have high contrast and are excellent in solvent resistance and electric reliability.

CITATION LIST

Patent Literature 1: International Publication No. WO2011/037195
Patent Literature 2: Japanese Patent Application Laid-Open No. 2012-233033
Patent Literature 3: International Publication No. WO2012/144521

SUMMARY OF INVENTION

Technical Problem

Since excellent heat resistance and high luminance can be expected, the inventors of the present invention studied the use of color materials described in Patent Literature 3. However, to adjust the color tones of the color materials to desired color tones, it is needed to use the color materials in combination with other color materials.

In the case of using conventionally-used dioxazine-based violet pigments as other color materials, due to low transmittance of the pigments, there is a problem of a decrease in luminance. In the case of using dyes, there is a problem of a decrease in heat resistance and light resistance, resulting in a decrease in luminance. In the case of using metal lake pigments, although the pigments have higher heat resistance than dyes, the pigments are still insufficient in heat resistance and result in a problem of a decrease in luminance.

The present invention was achieved in light of the above circumstances. An object of the present invention is to provide: a color material dispersion liquid which is able to form a high-luminance coating film having excellent heat resistance, with adjusting the color tone of the coating film to a desired color tone; a color resin composition for color filters, which is able to form a high-luminance color layer having excellent heat resistance, with adjusting the color tone of the color layer to a desired color tone; a high-luminance color filter using the color resin composition; a liquid crystal display device and an organic light-emitting display device each having the color filter; and a color material which has excellent heat resistance and is able to increase the temporal stability of the color resin composition.

Solution to Problem

The color material dispersion liquid according to the present invention includes: (A) a color material, (B) a dispersant and (C) a solvent, wherein the color material (A) includes a color material (A-1) in which at least a cation represented by the following general formula (I) and a monovalent anion represented by the following general formula (II) form a salt:

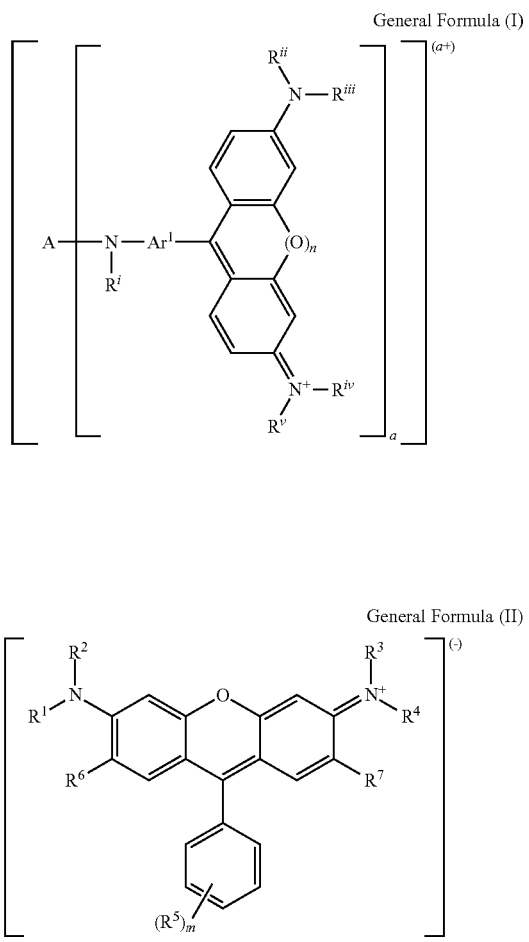

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$s can be the same or different; a plurality of $R^v$s can be the same or different; a plurality of $Ar^1$s can be the same or different;

"a" is a number of 2 or more; "n" is 0 or 1, and there is no bond when "n" is 0; and a plurality of "n"s can be the same or different; and wherein each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group ($—SO_3^-$ group) or a carboxylato group ($—COO^-$ group); m is 0 to 5; when there are a plurality of $R^5$s, they can be the same or different; each of $R^6$ and $R^7$ is independently a hydrogen atom, a halogen atom, or an alkyl group which can have a substituent group; and in $R^1$ to $R^5$, two sulfonato groups ($—SO_3^-$ groups) are contained, or one sulfonato group ($—SO_3^-$ group) and one carboxylato group ($—COO^-$ group) are contained.

The color resin composition for color filters according to the present invention includes: (A) a color material, (B) a dispersant, (C) a solvent and (D) a binder component, wherein the color material (A) contains a color material (A-1) in which at least a cation represented by the general formula (I) and a monovalent anion represented by the general formula (II) form a salt.

The color filter according to the present invention includes at least a transparent substrate and color layers disposed on the substrate, wherein at least one of the color layers contains a color material (A-1) in which at least a cation represented by the general formula (I) and a monovalent anion represented by the general formula (II) form a salt:

In the color material dispersion liquid according to the present invention, the color resin composition for color filters according to the present invention, and the color filter according to the present invention, from the viewpoint of heat resistance and dispersibility, it is preferable that the color material (A-1) is a color material which further contains a polyoxometalate anion and is represented by the following general formula (III):

General Formula (III)

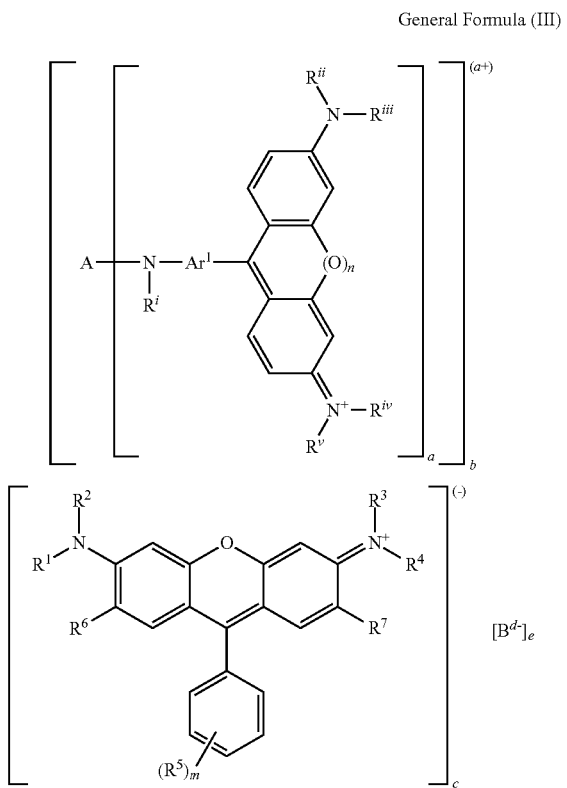

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$s can be the same or different; a plurality of $R^v$s can be the same or different; a plurality of $Ar^1$s can be the same or different;

"a" is a number of 2 or more; b is a number of 1 or more; "n" is 0 or 1, and there is no bond when "n" is 0; a plurality of "n"s can be the same or different;

each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group ($-SO_3^-$ group) or a carboxylato group ($-COO^-$ group); m is 0 to 5; when there are a plurality of $R^5$s, they can be the same or different; each of $R^6$ and $R^7$ is independently a hydrogen atom, a halogen atom, or an alkyl group which can have a substituent group;

in $R^1$ to $R^5$, two sulfonato groups ($-SO_3^-$ groups) are contained, or one sulfonato group ($-SO_3^-$ group) and one carboxylato group ($-COO^-$ group) are contained;

$B^{d-}$ is a "d"-valent polyoxometalate anion; and c and e are positive numbers.

In the color material dispersion liquid according to the present invention, the color resin composition for color filters according to the present invention, and the color filter according to the present invention, from the viewpoint of achieving both heat resistance and light resistance, it is preferable that the polyoxometalate anion in the color material represented by the general formula (III) contains at least tungsten, and a molar ratio of the tungsten to molybdenum in the polyoxometalate anion is 100:0 to 85:15.

The present invention provides a liquid crystal display device including the color filter according to the present invention, a counter substrate, and a liquid crystal layer disposed between the color filter and the counter substrate.

Also, the present invention provides an organic light-emitting display device including the color filter according to the present invention and an organic light-emitting material.

Also, the present invention provides a color material represented by the following general formula (III'):

General Formula (III')

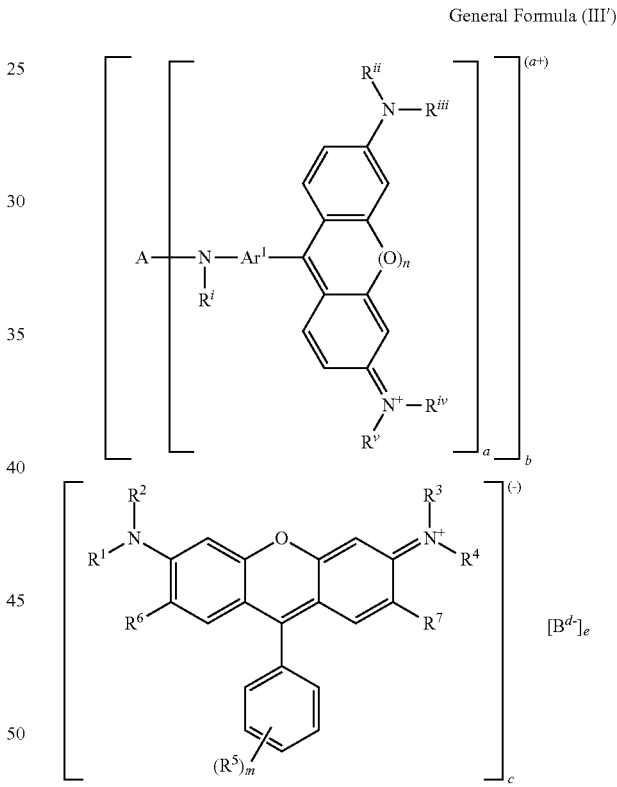

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$'s can be the same or different; a plurality of $R^v$'s can be the same or different; a plurality of $Ar^1$'s can be the same or different;

"a" is a number of 2 or more; b is a number of 1 or more; "n" is 0 or 1, and there is no bond when "n" is 0; a plurality of "n"s can be the same or different;

each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group (—$SO_3^-$ group) or a carboxylato group (—$COO^-$ group); m is 0 to 5; when there are a plurality of $R^5$s, they can be the same or different; each of $R^6$ and $R^7$ is independently a hydrogen atom, a halogen atom, or an alkyl group which can have a substituent group;

in $R^1$ to $R^5$, two sulfonato groups (—$SO_3^-$ groups) are contained, or one sulfonato group (—$SO_3^-$ group) and one carboxylato group (—$COO^-$ group) are contained;

$B^{d-}$ is a "d"-valent polyoxometalate anion; c and e are positive numbers; and c:(d×e) is 5:95 to 50:50.

Advantageous Effects of Invention

According to the present invention, the following can be provided: a color material dispersion liquid which is able to form a high-luminance coating film having excellent heat resistance, with adjusting the color tone of the coating film to a desired color tone; a color resin composition for color filters, which is able to form a high-luminance color layer having excellent heat resistance, with adjusting the color tone of the color layer to a desired color tone; a high-luminance color filter using the color resin composition; a liquid crystal display device and an organic light-emitting display device each having the color filter; and a color material which has excellent heat resistance and is able to increase the temporal stability of the color resin composition.

DESCRIPTION OF EMBODIMENTS

Figure 1:
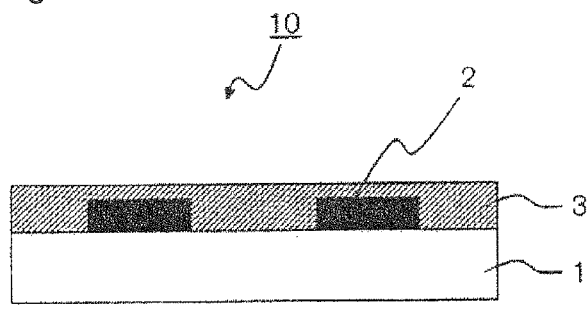
FIG. 1 is a schematic sectional view of an example of the color filter of the present invention.

Hereinafter, a color material dispersion liquid, a color material, a color resin composition for color filters, a color filter, a liquid crystal display device, and an organic light-emitting display device, which are according to the present invention, will be described in order.

In the present invention, "light" encompasses electromagnetic waves in visible and non-visible wavelength ranges and radial rays. Radial rays include microwaves and electron beams, more specifically, electromagnetic waves having a wavelength of 5 μm or less and electron beams.

Also in the present invention, "(meth)acrylic" means any of acrylic and methacrylic, and "(meth)acrylate" means any of acrylate and methacrylate.

Also in the present invention, "organic group" means a group having one or more carbon atoms.

1. Color Material Dispersion Liquid

The color material dispersion liquid according to the present invention includes: (A) a color material, (B) a dispersant and (C) a solvent, wherein the color material (A) contains a color material (A-1) in which at least a cation represented by the following general formula (I) and a monovalent anion represented by the following general formula (II) form a salt:

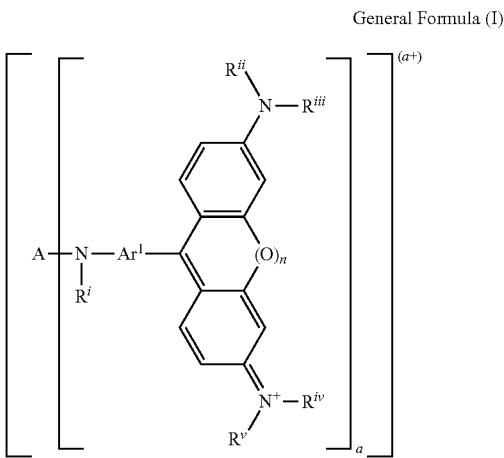

General Formula (I)

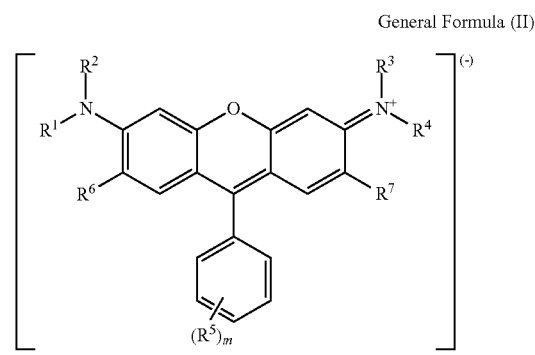

General Formula (II)

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$'s can be the same or different; a plurality of $R^{ii}$'s can be the same or different; a plurality of $R^{iii}$'s can be the same or different; a plurality of $R^{iv}$'s can be the same or different; a plurality of $R^v$'s can be the same or different; a plurality of $Ar^1$s can be the same or different;

"a" is a number of 2 or more; "n" is 0 or 1, and there is no bond when "n" is 0; and a plurality of "n"s can be the same or different; and wherein each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group ($—SO_3^-$ group) or a carboxylato group ($—COO^-$ group); m is 0 to 5; when there are a plurality of $R^5$s, they can be the same or different; each of $R^6$ and $R^7$ is independently a hydrogen atom, a halogen atom, or an alkyl group which can have a substituent group; and in $R^1$ to $R^5$, two sulfonato groups ($—SO_3^-$ groups) are contained, or one sulfonato group ($—SO_3^-$ group) and one carboxylato group ($—COO^-$ group) are contained.

In the color material dispersion liquid of the present invention, the above-specified color material (A-1) is used as the color material (A) and dispersed in the solvent (C). Therefore, the color material dispersion liquid becomes a color material dispersion liquid which is able to form a high-luminance coating film having excellent heat resistance, with adjusting the color tone of the coating film to a desired color tone.

The mechanism that the above-described effects are exerted by the above-specified combination is not clear yet; however, it is presumed as follows.

The cation represented by the general formula (I) has a plurality of color-forming moieties, and the color-forming moieties have a similar basic skeleton to that of basic dyes. Therefore, as with conventional dyes, the cation represented by the general formula (I) has excellent transmittance; meanwhile, the cation has a higher molecular weight and better heat resistance than conventional basic dyes. In the color material (A-1), such a cation represented by the general formula (I) and the monovalent anion represented by the general formula (II) form a salt. Therefore, it is presumed that the molecular weight and heat resistance of the color material are further increased, with adjusting the color tone of the color material dispersion liquid to a desired color tone, and high luminance can be achieved even after going through a high-temperature heating step included in a color filter production step.

A xanthene-based dye or lake pigment is less likely to be dispersed solely, so that a large amount of dispersant has been used. In the present invention, the color material (A-1) is dispersed by the dispersant (B) while the cation and the anion form a salt. Accordingly, compared to the case of separately dispersing a color material containing the cation represented by the general formula (I) and a color material containing the anion represented by the general formula (II), the amount of the dispersant used can be reduced. Therefore, the color material dispersion liquid of the present invention can be sufficiently dispersed even in the case where the content of the color material is increased; moreover, the color material dispersion liquid can become a color material dispersion liquid with high color density. Due to this reason, the range of design can be extended by the use of the color material dispersion liquid of the present invention, such as increasing the content of the binder component or other component in the color resin composition for color filters. Also, even in the case where the color material dispersion liquid is formed into a thinner coating film than ever before, a desired color tone can be obtained.

The color material dispersion liquid of the present invention contains at least the color material (A), the dispersant (B) and the solvent (C). It can further contain other components, as long as the effects of the present invention are not impaired.

Hereinafter, the components of such a color material dispersion liquid of the present invention will be described in detail.

[Color Material (A)]

The color material (A) used in the present invention contains the color material (A-1) in which at least the cation represented by the general formula (I) and the monovalent anion represented by the general formula (II) form a salt. It can further contain other color material, as long as the effects of the present invention are not impaired. In the present invention, by dispersing the color material (A-1) in which the cation represented by the general formula (I) and the monovalent anion represented by the general formula (II) form a salt, excellent dispersibility and heat resistance can be obtained; color density can be increased; and a high-luminance color filter can be obtained.

<Color Material (A-1)>

In the present invention, by using the color material (A-1) in which the cation represented by the following general formula (I) and the monovalent anion represented by the following general formula (II) form a salt as a color material, a higher-luminance color filter can be obtained; moreover, a color layer with excellent solvent resistance and electric reliability can be formed:

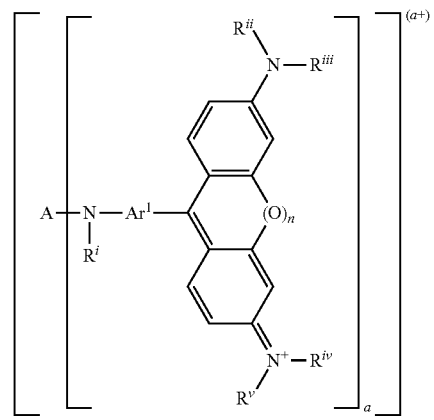

General Formula (I)

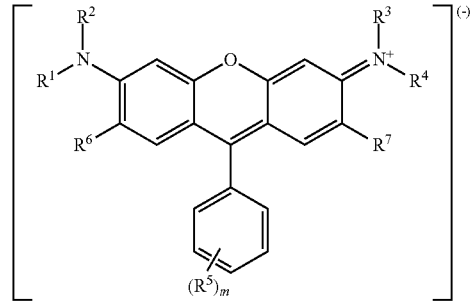

General Formula (II)

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$s can be the same or different; a plurality of $R^v$s can be the same or different; a plurality of $Ar^1$s can be the same or different;

"a" is a number of 2 or more; "n" is 0 or 1, and there is no bond when "n" is 0; and a plurality of "n"s can be the same or different; and wherein each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group ($-SO_3^-$ group) or a carboxylato group ($-COO^-$ group); m is 0 to 5; when there are a plurality of $R^5$s, they can be the same or different; each of $R^6$ and $R^7$ is independently a hydrogen atom, a halogen atom, or an alkyl group which can have a substituent group; and in $R^1$ to $R^5$, two sulfonato groups ($-SO_3^-$ groups) are contained, or one sulfonato group ($-SO_3^-$ group) and one carboxylato group ($-COO^-$ group) are contained.

Figure 4:
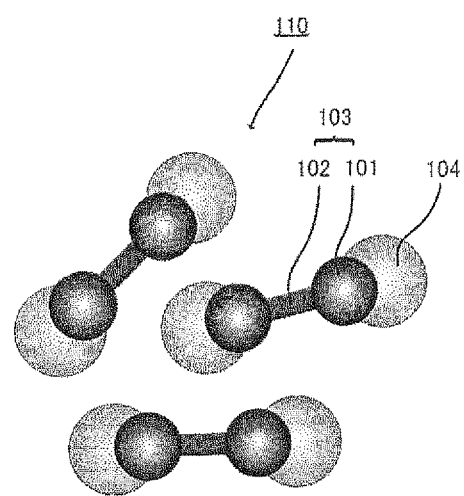
FIG. 4 is a schematic view of an example of a color material (A-1).

A schematic view of the color material (A-1) is shown in FIG. 4. In a color material 110, which is the color material (A-1), a cation 103 represented by the general formula (I), in which a plurality of color-forming moieties 101 are connected through a linking group A (102), and monovalent anions 104 represented by the general formula (II) form a salt. Since the color-forming moieties 101 of the cation 103 represented by the general formula (I) are cationic moieties, it is presumed that the monovalent anions 104 represented by the general formula (II) form ion pairs with the color-forming moieties 101. Since the color-forming moieties 101 and the monovalent anions 104 represented by the general formula (II) are similar in carbon skeleton, such as having an aromatic ring, it is presumed that ion pair dissociation is inhibited by an interaction such as π-π interaction. As a result, it is presumed that heat resistance is further increased.

(Cation Represented by the General Formula (I))

The color material (A-1) used in the present invention has the cation represented by the following general formula (I). Due to containing the cation, the color material (A-1) has excellent heat resistance.

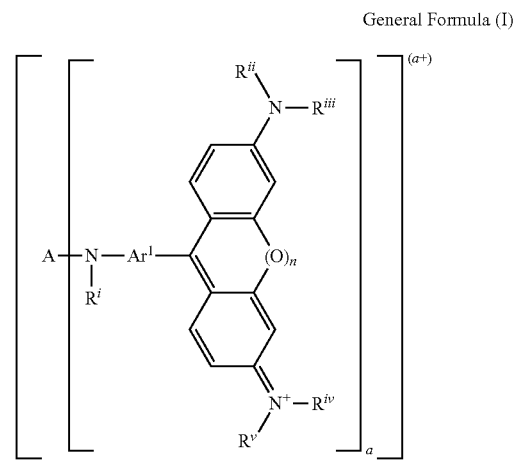

General Formula (I)

(Symbols in the general formula (I) are as described above.)

In the general formula (I), A is an "a"-valent organic group in which a carbon atom directly bound to N (nitrogen atom) has no π bond. The organic group is an aliphatic hydrocarbon group having a saturated aliphatic hydrocarbon group at least at a terminal position directly bound to N, or an aromatic group having the aliphatic hydrocarbon group, and O (oxygen atom), S (sulfur atom), N (nitrogen atom) can be contained in a carbon chain of the organic group. Since the carbon atom directly bound to N has no π bond, the color characteristics of the cationic color-forming moiety, such as color tone and transmittance, are not affected by the linking group A and other color-forming moieties, thereby allowing the same color as that of a single color-forming moiety.

In A, as long as the carbon atom being at the terminal position and directly bound to N has no π bond, the aliphatic hydrocarbon group having a saturated aliphatic hydrocarbon group at least at a terminal position directly bound to N, can be in a straight-chain, branched-chain or cyclic form, have an unsaturated bond in carbon atoms except the one in the terminal position, have a substituent group, or contain O, S, N in the carbon chain. For example, a carbonyl group, a carboxyl group, an oxycarbonyl group and/or an amide group can be contained, and a hydrogen atom can be substituted by a halogen atom, etc.

Also in A, as the aromatic group having an aliphatic hydrocarbon group, there may be exemplified a monocyclic or polycyclic aromatic group which has an aliphatic hydrocarbon group having a saturated aliphatic hydrocarbon group at least at the terminal position directly bound to N. The aromatic group can have a substituent group, and it can be a heterocyclic ring containing O, S, N.

Particularly, from the viewpoint of skeleton toughness, it is preferable that A contains a cyclic aliphatic hydrocarbon group or an aromatic group.

As the cyclic aliphatic hydrocarbon group, a bridged alicyclic hydrocarbon group is particularly preferable from the viewpoint of skeleton toughness. The bridged alicyclic hydrocarbon group refers to a polycyclic aliphatic hydrocarbon group having a bridged structure in the aliphatic ring and having a polycyclic structure. The examples include norbornane, bicyclo[2,2,2]octane and adamantane. Of bridged alicyclic hydrocarbon groups, norbornane is preferable. Examples of the aromatic group include groups containing a benzene ring and those containing a naphthalene ring. Of them, groups containing a benzene ring are preferable. In A, the valence "a" refers to the number of cationic color-forming moieties constituting the cation, and "a" is a number of 2 or more. Because the valence "a" of the cation is 2 or more, the color material of the present invention has excellent heat resistance. The upper limit of "a" is not particularly limited. From the viewpoint of ease of production, "a" is preferably 2 to 4, more preferably 2 to 3, still more preferably 2. For example, when A is a divalent organic group, examples of the divalent organic group include a straight-chain, branched-chain or cyclic alkylene group having 1 to 20 carbon atoms, and an aromatic group in which two alkylene groups each having 1 to 20 carbon atoms are bound by substitution, such as a xylylene group.

The alkyl group as each of $R^i$ to $R^v$ is not particularly limited. Examples of the alkyl group include a straight- or branched-chain alkyl group having 1 to 20 carbon atoms. Of them, preferred is a straight- or branched-chain alkyl group having 1 to 8 carbon atoms, and more preferred is a straight- or branched-chain alkyl group having 1 to 5 carbon atoms, from the viewpoint of luminance and heat resistance. Of them, still more preferred is an ethyl group or a methyl group. A substituent group that the alkyl group can have is not particularly limited. The examples include an aryl group, a halogen atom and a hydroxyl group. As the substituted alkyl group, a benzyl group can be exemplified.

The aryl group as each of $R^i$ to $R^v$ is not particularly limited. The examples include a phenyl group and a naphthyl group. As a substituent group that the aryl group can have, an alkyl group and a halogen atom can be exemplified.

"$R^{ii}$ and $R^{iii}$ can be bound to form a ring structure, and/or $R^{iv}$ and $R^v$ can be bound to form a ring structure" means that $R^{ii}$ and $R^{iii}$ form a ring structure through a nitrogen atom, and/or $R^{iv}$ and $R^v$ form a ring structure through a nitrogen atom. The ring structure is not particularly limited, and the examples include a pyrrolidine ring, a piperidine ring and a morpholine ring.

Particularly, from the viewpoint of chemical stability, it is preferable that each of $R^i$ to $R^v$ is independently a hydrogen atom, an alkyl group having 1 to 5 carbon atoms, or a phenyl group. Or, it is preferable that $R^{ii}$ and $R^{iii}$ are bound to form a pyrrolidine ring, a piperidine ring or a morpholine ring, and/or $R^{iv}$ and $R^v$ are bound to form a pyrrolidine ring, a piperidine ring or a morpholine ring.

Each of $R^i$ to $R^v$ can independently have the above structure. Particularly, from the viewpoint of color purity, it is preferable that $R^i$ is a hydrogen atom. From the viewpoint of ease of production and availability of raw materials, it is more preferable that all of $R^{ii}$ to $R^v$ are the same.

The divalent aromatic group as $Ar^1$ is not particularly limited. The aromatic group as $Ar^1$ can be the same as those described above as the aromatic group as A.

$Ar^1$ is preferably an aromatic group having 6 to 20 carbon atoms, more preferably an aromatic group having a condensed polycyclic carbon ring having 10 to 14 carbon atoms. Still more preferred are a phenylene group and a naphthylene group, from the point of view that the structure is simple and the raw materials are low-cost.

A plurality of $R^i$s per molecule can be the same or different; a plurality of $R^{ii}$s per molecule can be the same or different; a plurality of $R^{iii}$s per molecule can be the same or different; a plurality of $R^{iv}$s per molecule can be the same or different; a plurality of $R^v$s per molecule can be the same or different; and a plurality of $Ar^1$s per molecule can be the same or different. Depending on the combination of $R^i$ to $R^v$ and $Ar^1$, it is possible to produce a desired color.

In the general formula (I), "n" is an integer of 0 or 1. In the general formula (I), "n=0" indicates a triarylmethane skeleton, and "n=1" indicates a xanthene skeleton. In the general formula (I), a plurality of "n"s can be the same or different. The examples include a cation having a plurality of triarylmethane or xanthene skeletons only, and a cation having both triarylmethane and xanthene skeletons per molecule. From the viewpoint of color purity, the cation having the same skeletons only is preferred. On the other hand, by having the cation including both triarylmethane and xanthene skeletons, it is possible to adjust the color of the cation represented by the general formula (I) to a desired color.

The method for producing the cation represented by the general formula (I) can be appropriately selected from conventionally-known methods. For example, it can be obtained by the production method described in International Publication No. WO2012/144521.

(Monovalent Anion Represented by the General Formula (II))

The color material (A-1) used in the present invention has the monovalent anion represented by the following general formula (II). By allowing the monovalent anion to form a salt with the cation represented by the general formula (I), it is possible to increase heat resistance, to adjust the color tone of a color layer to a desired color tone, and to achieve higher luminance.

General Formula (II)

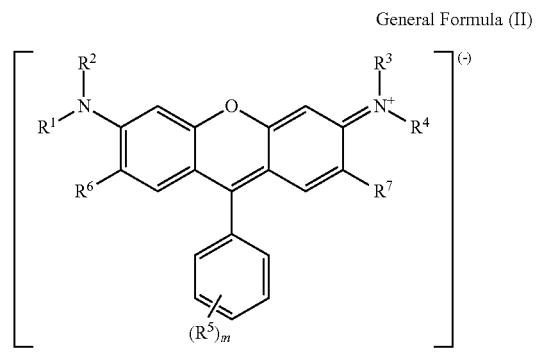

(Symbols in the general formula (II) are as described above.)

Examples of the alkyl group as each of $R^1$ to $R^4$ include a straight- or branched-chain alkyl group having 1 to 12 carbon atoms. Of them, preferred is a straight- or branched-chain alkyl group having 1 to 8 carbon atoms, and more preferred is a straight- or branched-chain alkyl group having 1 to 5 carbon atoms, from the viewpoint of luminance and heat resistance. Of them, still more preferred is an ethyl group or a methyl group. A substituent group that the alkyl group can have is not particularly limited. The examples include an aryl group, a halogen atom, a hydroxyl group, a substituent group containing a sulfonato group ($-SO_3^-$ group), and a substituent group containing a carboxylato group ($-COO^-$ group). As the substituted alkyl group, a benzyl group can be exemplified. The substituted alkyl group can further have a sulfonato group or carboxylato group.

Examples of the aryl group as each of $R^1$ to $R^4$ include an aryl group having 6 to 12 carbon atoms. Concrete examples of the aryl group include a phenyl group and a naphthyl group. As a substituent group that the aryl group can have, an alkyl group and a halogen atom can be exemplified. The alkyl group can further have a sulfonato group or carboxylato group.

Examples of the aralkyl group as each of $R^1$ to $R^4$ include an aralkyl group having 7 to 16 carbon atoms. Concrete examples thereof include a benzyl group, a phenethyl group, a naphthylmethyl group and a biphenylmethyl group. The aralkyl group can further have a sulfonato group or carboxylato group.

"R¹ and R² can be bound to form a ring structure, and/or R³ and R⁴ can be bound to form a ring structure" means that R¹ and R² form a ring structure through a nitrogen atom, and/or R³ and R⁴ form a ring structure through a nitrogen atom. The ring structure is not particularly limited, and the examples include a pyrrolidine ring, a piperidine ring and a morpholine ring.

The alkyl group as each of $R^6$ and $R^7$ can be the same as the above-mentioned alkyl group as each of $R^1$ to $R^4$. Examples of the halogen atom as each of $R^6$ and $R^7$ include a fluorine atom, a chlorine atom, a bromine atom and an iodine atom.

$R^5$ is a halogen atom, an alkyl group which can have a substituent group, a sulfonato group (—$SO_3^-$ group) or a carboxylato group (—$COO^-$ group). The alkyl group which can have a substituent group can be the same as the above-mentioned alkyl group as each of $R^1$ to $R^4$. The alkyl group can have a sulfonato group or carboxylato group.

In the general formula (II), from the viewpoint of stability, the substitution position of the substituent group $R^5$ in the benzene ring attached to the xanthene skeleton, is preferably the ortho- or para-position, more preferably in the ortho-position, with respect to the xanthene skeleton. It is presumed that when the substituent group $R^5$ is in the ortho-position, it resonates with the carbon atoms of the xanthene skeleton to which the benzene ring attaches, thus being able to form a ring structure and increasing heat resistance and light resistance.

In the anion represented by the general formula (II) of the present invention, a total of two sulfonato groups (—$SO_3^-$ groups) per molecule are contained in $R^1$ to $R^5$ per molecule, or one sulfonato group (—$SO_3^-$ group) and one carboxylato group (—$COO^-$ group) are contained in $R^1$ to $R^5$ per molecule. Accordingly, the anion represented by the general formula (II) is a monovalent anion. Because the anion represented by the general formula (II) is a monovalent anion, the molecular weight of the color material (A-1) is an appropriate weight, as shown in FIG. 4, and the color material (A-1) is excellent in dispersibility.

Concrete examples of the monovalent anion represented by the general formula (II) include anions such as anions of Acid Red 50, 52 and 289, Acid Violet 9 and 30, and Acid Blue 19. From the viewpoint of excellent heat resistance, being able to form a high-luminance coating film, and availability, Acid Red 52 and 289 are preferably used.

(Other Ions)

The color material (A-1) can further contain other cation or anion and be a double salt, to the extent that does not impair the effect of the present invention. Concrete examples of such a cation include other basic dyes, organic compounds containing a functional group which is able to form a salt with an anion, such as an amino group, pyridine group or imidazole group, metal ions such as a sodium ion, potassium ion, magnesium ion, calcium ion, copper ion, iron ion, aluminum ion and zirconium ion, and inorganic polymers such as polyaluminum chloride. Concrete examples of such an anion include halide ions such as a fluoride ion, chloride ion and bromide ion, and inorganic acid anions. Examples of the inorganic acid anions include oxo acid anions such as a phosphate ion, sulfate ion, chromate ion, tungstate ion ($WO_4^{2-}$) and molybdate ion ($MoO_4^{2-}$), and polyoxometalate anion. In the present invention, it is particularly preferable that the color material (A-1) is a color material which further contains a polyoxometalate anion and is represented by the following general formula (III), because a high-luminance coating film having excellent heat resistance can be formed:

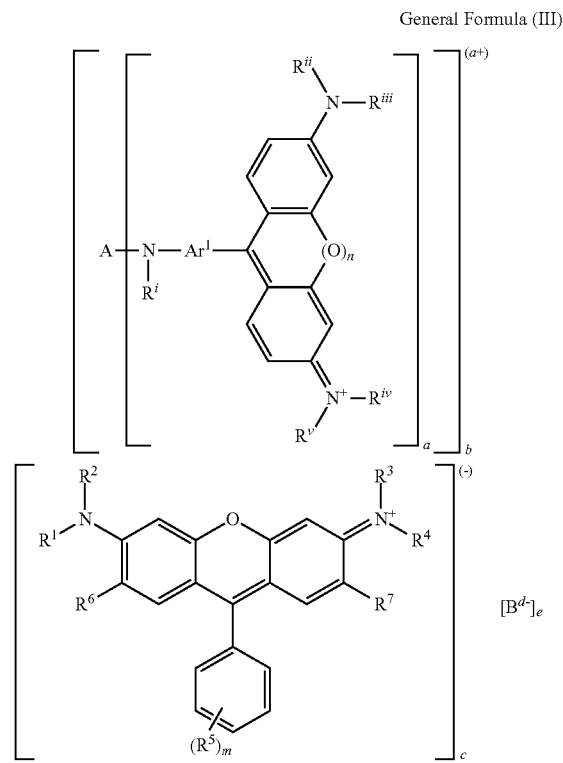

General Formula (III)

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$s can be the same or different; a plurality of $R^v$s can be the same or different; a plurality of $Ar^1$s can be the same or different;

"a" is a number of 2 or more; b is a number of 1 or more; "n" is 0 or 1, and there is no bond when "n" is 0; a plurality of "n"s can be the same or different;

each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group (—$SO_3^-$ group) or a carboxylato group (—$COO^-$ group); m is 0 to 5; when there are a plurality of $R^5$s, they can be the same or different; each of $R^6$ and $R^7$ is independently a hydrogen atom, a halogen atom, or an alkyl group which can have a substituent group;

in $R^1$ to $R^5$, two sulfonato groups (—$SO_3^-$ groups) are contained, or one sulfonato group (—$SO_3^-$ group) and one carboxylato group (—$COO^-$ group) are contained;

$B^{d-}$ is a "d"-valent polyoxometalate anion; and c and e are positive numbers.

Figure 5:
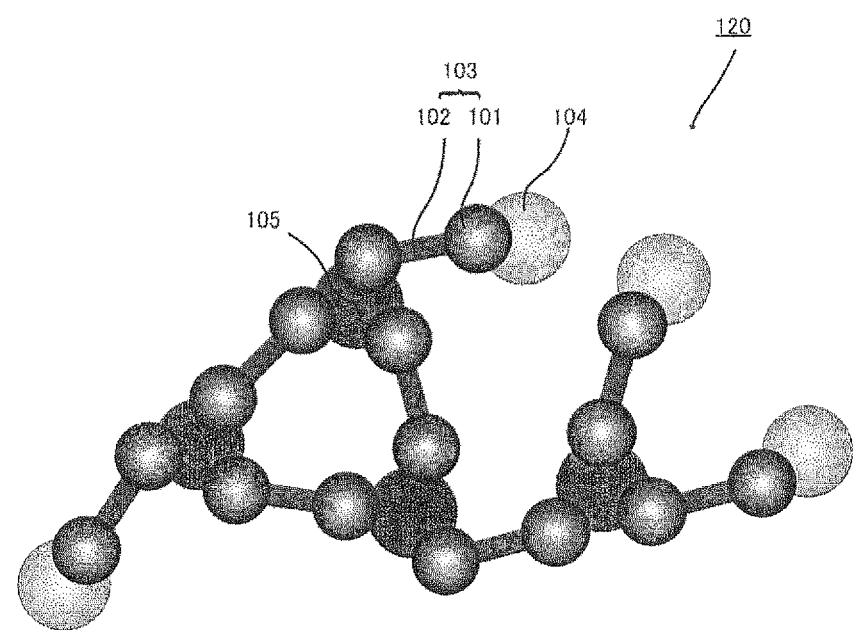
FIG. 5 is a schematic view of a different example of the color material (A-1).

FIG. 5 is a schematic view of the color material represented by the general formula (III). In a color material 120 represented by the general formula (III), a cation 103 represented by the general formula (I), in which a plurality of color-forming moieties 101 are connected through a linking group A (102), a monovalent anion 104 represented by the general formula (II), and a polyoxometalate anion 105 form a salt. Due to containing the divalent or higher polyoxometalate anion 105 and the divalent or higher cation 103, it is presumed that a molecular association is formed in the color material represented by the general formula (III), in which a plurality of molecules associate through the polyoxometalate anion 105. Therefore, it is presumed that the apparent molecular weight of the color material represented by the general formula (III) is increased much higher than the molecular weight of conventional lake pigments, and the cohesion in a solid state is further increased; ion pair dissociation and dye skeleton decomposition can be inhibited; and heat resistance is increased. It is also presumed that by the use of the polyoxometalate anion 105, which is an inorganic anion, as the divalent or higher anion, connections between the molecular associations are consolidated, so that heat resistance is further increased.

On the other hand, the cation represented by the general formula (I) also forms a salt with the monovalent anion 104 represented by the general formula (II), and the salt-forming moiety constitutes a terminal position of the molecular association. Therefore, the size of the molecular associations are prevented from becoming too large, and the color material represented by the general formula (III) obtains excellent heat resistance and a size excellent for dispersion. As a result, it is presumed that the amount of the dispersant used can be decreased; the concentration of the color material in the color material dispersion liquid can be relatively increased; and even if a thin color layer is formed, the color tone of the color layer can be adjusted to a desired color tone.

$R^i$ to $R^v$, A, $Ar^1$, "a" and "n" in the general formula (III) can be the same as those in the general formula (I). $R^1$ to $R^7$ and "m" in the general formula (III) can be the same as those in the general formula (II).

In the general formula (III), the polyoxometalate anion ($B^{d-}$) can be isopolyoxometalate ion $(M_mO_n)^{d-}$ or heteropolyoxometalate ion $(X_lM_mO_n)^{d-}$. In the ionic formulae, M is a polyatom; X is a heteroatom; "m" is the compositional ratio of the polyatom; and "n" is the compositional ratio of an oxygen atom. As the polyatom (M), there may be mentioned Mo, W, V, Ti, Nb, etc. As the heteroatom (X), there may be mentioned Si, P, As, S, Fe, Co, etc. A counter cation such as $Na^+$ or $H^+$ can be contained in a part of the polyoxometalate anion.

From the viewpoint of high luminance and excellent heat resistance and light resistance, preferred is a polyoxometalate anion containing at least one of tungsten (W) and molybdenum (Mo). From the viewpoint of heat resistance, more preferred is a polyoxometalate anion which contains at least tungsten and can contain molybdenum.

As the polyoxometalate anion containing at least one of tungsten (W) and molybdenum (Mo), for example, there may be mentioned a tungstate ion $[W_{10}O_{32}]^{4-}$ and a molybdate ion $[Mo_6O_{19}]^{2-}$, which are isopolyoxometalates, and phosphotungstate ions $[PW_{12}O_{40}]^{3-}$ and $[P_2W_{18}O_{62}]^{6-}$, a silicotungstate ion $[SiW_{12}O_{40}]^{4-}$, a phosphomolybdate ion $[PMo_{12}O_{40}]^{3-}$, a silicomolybdate ion $[SiMo_{12}O_{40}]^{4-}$, phosphotungstic molybdate ions $[PW_{12-x}Mo_xO_{40}]^{3-}$ (x is an integer of 1 to 11) and $[P_2W_{18-y}Mo_yO_{62}]^{6-}$ (y is an integer of 1 to 17) and a silicotungstic molybdate ion $[SiW_{12-x}Mo_xO_{40}]^{4-}$ (x is an integer of 1 to 11), which are all heteropolyoxometalates. Of these examples, from the viewpoint of heat resistance and availability of raw materials, the polyoxometalate anion containing at least one of tungsten (W) and molybdenum (Mo) is preferably a heteropolyoxometalate, more preferably a heteropolyoxometalate containing phosphorus (P).

In the polyoxometalate anion containing at least tungsten (W), the content ratio of the tungsten to molybdenum is not particularly limited. Particularly from the viewpoint of excellent heat resistance, the molar ratio of the tungsten to molybdenum is preferably 100:0 to 85:15, more preferably 100:0 to 90:10.

In the general formula (III), as the polyoxometalate anion, the above-mentioned polyoxometalate anions can be used alone or in combination of two or more kinds. In the case of using a combination of two or more kinds of the above-mentioned polyoxometalate anions, the molar ratio of the tungsten to molybdenum in the whole polyoxometalate anion is preferably in the above range.

In the color material represented by the general formula (III), the content ratio of the anion represented by the general formula (II) to the polyoxometalate anion can be appropriately adjusted so as to obtain a desired color tone. From the viewpoint of heat resistance and dispersibility, the charge-based content ratio (c:(d×e)) of the anion represented by the general formula (II) to the "d"-valent polyoxometalate anion is preferably 5:95 to 40:60, more preferably 10:90 to 30:70.

In the present invention, the color material (III) is particularly preferably a color material represented by the following general formula (III'), from the viewpoint of excellent heat resistance and being able to increase the temporal stability of the below-described color resin composition.

General Formula (III')

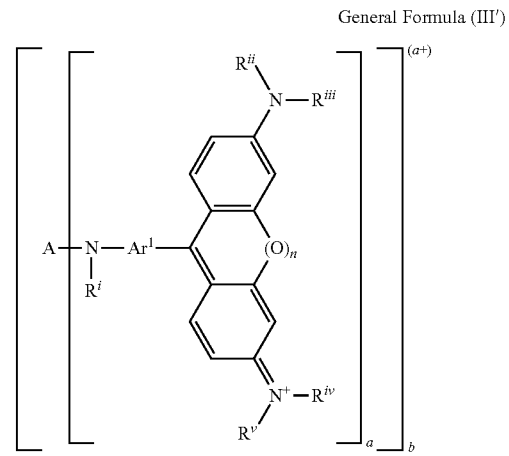

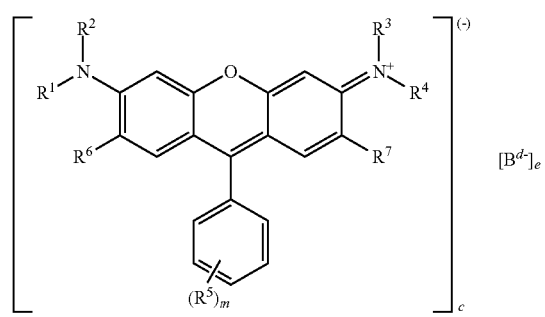

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$s can be the same or different; a plurality of $R^v$s can be the same or different; a plurality of $Ar^1$s can be the same or different;

"a" is a number of 2 or more; b is a number of 1 or more; "n" is 0 or 1, and there is no bond when "n" is 0; a plurality of "n"s can be the same or different;

each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group (—$SO_3^-$ group) or a carboxylato group (—$COO^-$ group); m is 0 to 5; when there are a plurality of $R^5$s, they can be the same or different; each of $R^6$ and $R^7$ is independently a hydrogen atom, a halogen atom, or an alkyl group which can have a substituent group;

in $R^1$ to $R^5$, two sulfonato groups (—$SO_3^-$ groups) are contained, or one sulfonato group (—$SO_3^-$ group) and one carboxylato group (—$COO^-$ group) are contained;

$B^{d-}$ is a "d"-valent polyoxometalate anion; c and e are positive numbers; and c:(d×e) is 5:95 to 50:50.

As a result of diligent research, the inventors of the present invention have found that excellent heat resistance and a color resin composition with excellent temporal stability can be obtained by, in the color material represented by the general formula (III), adjusting the charge-based content ratio of the anion represented by the general formula (II), which is a monovalent anion, to the "d"-valent polyoxometalate anion, within a range of 5:95 to 50:50, that is, by adjusting (1×c):(d×e) to be in a range of 5:95 to 50:50.

Figure 6:
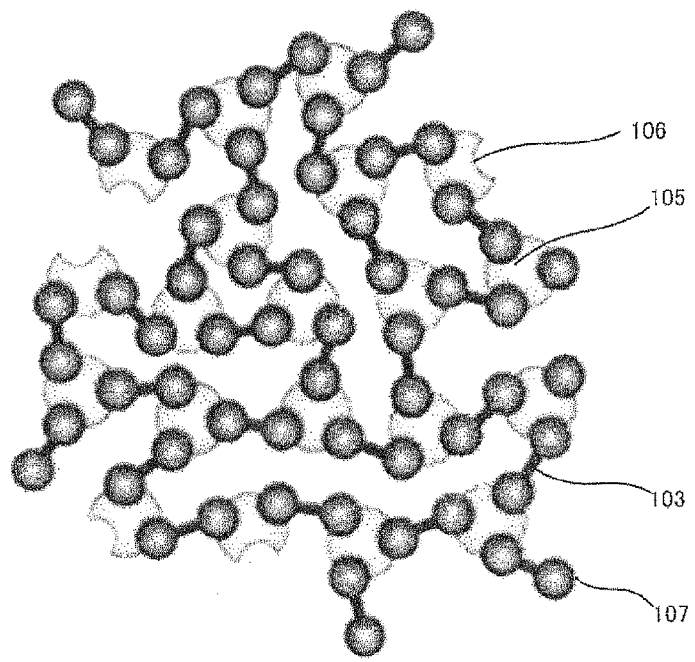
FIG. 6 is a schematic view of an example of a color material in which a cation represented by the general formula (I) and a polyoxometalate anion form a salt.
Figure 7:
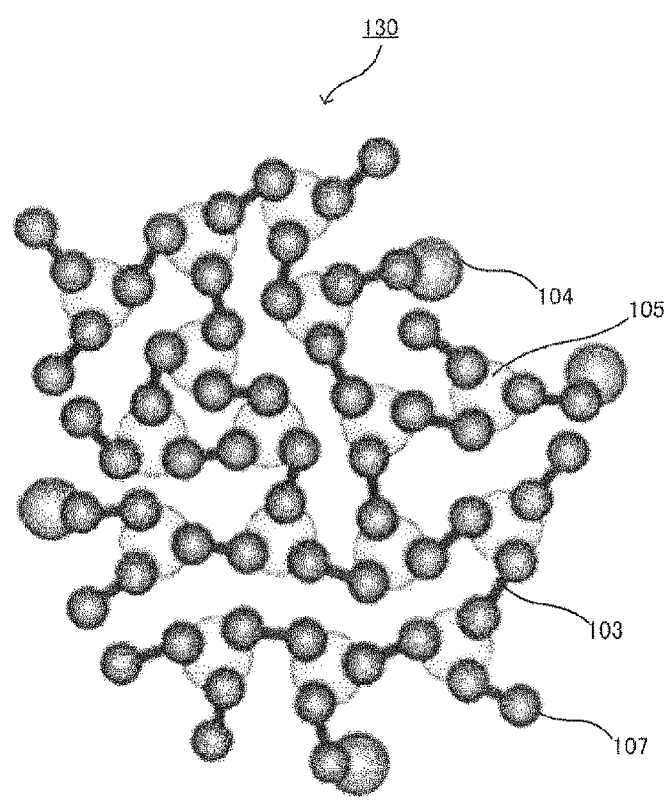
FIG. 7 is a schematic view of an example of a color material represented by the general formula (III').

This finding will be further described with reference to figures. FIG. 6 is a schematic view of an example of the color material in which the cation represented by the general formula (I) and the polyoxometalate anion form a salt. FIG. 7 is a schematic view of an example of the color material represented by the general formula (III'). As described above, it is presumed that the molecular association is formed by combining the divalent or higher cation with the divalent or higher anion. However, as shown by the example in FIG. 6, in the case where only the cations 103 represented by the general formula (I) and the polyoxometalate anions 105 are combined, it is presumed that the polyoxometalate anion 106 not forming a salt or the cation 107 being represented by the general formula (I) and not forming a salt, is present at a terminal position of the molecular association. The polyoxometalate anion 106 not forming a salt is highly acidic, and when it is present at a terminal position of the molecular association, it is presumed that the polyoxometalate anion acts on the below-described binder component or the like and decomposes or denaturalizes it. Therefore, it is presumed that the color material as shown by the example in FIG. 6 is likely to increase the viscosity of the below-described color resin composition over time, when it is formed into the below-described color resin composition.

On the other hand, as shown by the example in FIG. 7, in the color material 130 represented by the general formula (III'), by combining the monovalent anion 104 represented by the general formula (II) with the polyoxometalate anion 105 in specific amounts, the molecular association with increased heat resistance is formed and, at the same time, the content of the polyoxometalate anion 105 is relatively small. Therefore, it is presumed that the ratio of the polyoxometalate anion 106 not forming a salt decreases, so that reaction with the binder component is inhibited. Due to the above reasons, the color resin composition using the color material represented by the general formula (III') is also excellent in temporal stability.

In the present invention, the content ratio (c:(d×e)) of the anion represented by the general formula (II) to the "d"-valent polyoxometalate anion is preferably 5:95 to 40:60, more preferably 10:90 to 30:70.

The method for producing the color material (A-1) can be appropriately selected from conventionally-known methods. For example, the color material can be obtained by mixing the cation represented by the general formula (I), the anion represented by the general formula (II), and other ions used as needed, such as polyoxometalate anion, in a solvent.

<Other Color Material>

In order to adjust color tone, the color material (A) can further contain other color material, to the extent that does not impair the effects of the present invention. As the other color material, there may be mentioned known pigments and dyes, etc., and they can be used alone or in combination of two or more kinds. As the other color material, it is particularly preferable to use the color material described in International Publication No. WO 2012/144521, which contains the divalent or higher cation represented by the general formula (I) and a divalent or higher anion. Concrete examples of the other color material and the content of the other color material are not particularly limited, as long as the effects of the present invention are not impaired, and can be the same as the case of the below-described color resin composition for color filters.

In the present invention, the average dispersed particle diameter of the color material (A) used is not particularly limited, as long as a desired color can be obtained when the color material is formed into the color layer of a color filter. From the viewpoint of increasing contrast and obtaining excellent heat resistance and light resistance, the average dispersed particle diameter is preferably in a range of 10 to 200 nm, more preferably in a range of 20 to 150 nm. By setting the average dispersed particle diameter of the color material (A) within the range, the liquid crystal display device and organic light-emitting display device produced by using the color resin composition for color filters according to the present invention, can have high contrast and high quality.

The average dispersed particle diameter of the color material (A) in the color material dispersion liquid is the dispersed particle diameter of the color material particles dispersed in a dispersion medium that contains at least a solvent, and it is measured with a laser scattering particle size distribution analyzer. The average dispersed particle diameter can be measured as follows with a laser scattering particle size distribution analyzer: the color material dispersion liquid is appropriately diluted with the solvent used for the color material dispersion liquid to a concentration that is measurable with a laser scattering particle size distribution analyzer (e.g., 1,000-fold) and then measured with a laser scattering particle size distribution analyzer (e.g., Nanotrac Particle Size Analyzer UPA-EX150 manufactured by Nikkiso Co., Ltd.) by a dynamic light scattering method at 23° C. This average dispersed particle diameter is a volume average particle diameter.

In the color material dispersion liquid of the present invention, the content of the color material is not particularly limited. From the viewpoint of dispersibility and dispersion stability, the content of the color material is preferably in a range of 5 to 40% by mass, more preferably 10 to 20% by mass, with respect to the total amount of the color material dispersion liquid.

[(B) Dispersant]

In the color material dispersion liquid of the present invention, the color material (A-1) is dispersed in the solvent by the dispersant (B) for use. The dispersant (B) can be selected from those that are conventionally used as dispersants. Concrete examples of the dispersant include surfactants such as cationic, anionic, nonionic, amphoteric, silicone-based and fluorine-based dispersing agents. Among surfactants, polymer surfactants (polymer dispersants) are preferred from the viewpoint of being able to disperse the color material homogeneously and finely.

Examples of polymer dispersants include: (co)polymers of unsaturated carboxylic acid esters such as polyacrylic acid ester; (partial) amine salts, (partial) ammonium salts and (partial) alkylamine salts of (co)polymers of unsaturated carboxylic acids such as polyacrylic acid; (co)polymers of hydroxyl group-containing unsaturated carboxylic acid esters such as hydroxyl group-containing polyacrylic acid ester, and modified products thereof; polyurethanes; unsaturated polyamides; polysiloxanes; long-chain polyaminoamide phosphates; polyethyleneimine derivatives (amide and bases thereof, obtained by reaction of poly(lower alkylenelmine) and polyester having a free carboxyl group); and polyallylamine derivatives (reaction products obtained by reaction of polyallylamine and one or more compounds selected from the group consisting of the following three kinds of compounds: polyester having a free carboxyl group, polyamide, and a co-condensate of ester and amide (polyester amide).

Commercially-available products of such dispersants include Disperbyk-2000 and 2001, and BYK-LPN 6919 and 21116 (all manufactured by BYK Japan KK), AJISPER PB821 and 881 (manufactured by Ajinomoto Co., Inc.) and so on. Of them, BYK-LPN 6919 and 21116 are preferred from the viewpoint of heat resistance, electric reliability and dispersibility.

From the point of view that appropriate dispersion of the color material (A-1) and excellent dispersion stability can be achieved, the polymer dispersant is particularly preferably one or more kinds selected from the group consisting of a polymer having at least a constitutional unit represented by the following general formula (IV) and urethane-based dispersants composed of compounds having one or more urethane bonds (—NH—COO—) per molecule.

Hereinafter, the preferred dispersant will be described in detail.

<Polymer Having at Least a Constitutional Unit Represented by the Following General Formula (IV)>

In the present invention, a polymer having at least a constitutional unit represented by the following general formula (IV) can be preferably used as the dispersant (B):

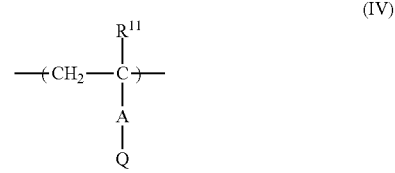

(IV)

wherein $R^{11}$ is a hydrogen atom or a methyl group; A is a direct bond or a divalent linking group; Q is a group represented by the following general formula (IV-a) or a nitrogen-containing heterocyclic group which is able to form a salt and which can have a substituent group:

(IV-a)

wherein each of $R^{12}$ and $R^{13}$ is independently a hydrogen atom or a hydrocarbon group which can contain a heteroatom, and $R^{12}$ and $R^{13}$ can be the same or different from each other.

In the general formula (IV), A is a direct bond or a divalent linking group. The direct bond means that Q is directly bound to a carbon atom in the general formula (IV), not through a linking group.

Examples of the divalent linking group as A include an alkylene group having 1 to 10 carbon atoms, an arylene group, a —CONH— group, a —COO— group, an ether group having 1 to 10 carbon atoms (—R'—OR"— where each of R' and R" is independently an alkylene group) and combinations thereof.

From the viewpoint of dispersibility, A in the general formula (IV) is preferably a direct bond or a divalent linking group containing a —CONH— group or a —COO— group.

The above dispersants can be particularly preferably used by allowing the constitutional unit represented by the general formula (IV) of the dispersants to form a salt by the below-described salt forming agent, at a desired ratio.

As the polymer having the constitutional unit represented by the general formula (IV), block and graft copolymers having structures disclosed in International Publication No. WO2011/108495 and Japanese Patent Application Laid-Open (JP-A) Nos. 2013-054200, 2010-237608 and 2011-75661 are particularly preferred, from the point of view that the dispersibility and dispersion stability of the color material and the heat resistance of the resin composition can be increased, and a color layer with high luminance and high contrast can be formed.

Commercially-available products of the polymers having the constitutional unit represented by the general formula (IV) include BYK-LPN 6919.

(Salt Forming Agent)

In the present invention, the dispersant is preferably a polymer in which at least a part of a nitrogen site of the constitutional unit represented by the general formula (IV) forms a salt (hereinafter, this state may be referred to as "salt-modified").

In the present invention, by allowing the nitrogen site of the constitutional unit represented by the general formula (IV) to form a salt using the salt forming agent, the dispersant strongly adsorbs to the color material similarly forming a salt, so that the dispersibility and dispersion stability of the color material are increased. As the salt forming agent, acidic organophosphorus compounds, organic sulfonic acid compounds and quaternizing agents, which are disclosed in International Publication No. WO2011/108495 and JP-A No. 2013-054200, can be preferably used. Especially when the salt forming agent is an acidic organophosphorus compound, salt-forming moieties containing the acidic organophosphorus compound of the dispersant are localized on the surface of the color material particles, and thus the color material surface reaches a state of being covered with phosphate. Therefore, attacks on the dye skeleton of the color material by active oxygen (hydrogen abstraction) are inhibited, so that the heat resistance and light resistance of the color material containing the dye skeleton are increased. For this reason, color deterioration by high-temperature heating can be further inhibited by using the polymer salt-modified by the acidic organophosphorus compound as the dispersant, while the color material (A) having high transmittance and being used in the present invention is in a state of being sufficiently dispersed. Therefore, a color layer which shows higher luminance even after the high-temperature heating step included in the color filter production step, can be formed.

<Urethane-Based Dispersant>

The urethane-based dispersant which is preferably used as the dispersant, is a dispersant composed of a compound having one or more urethane bonds (—NH—COO—) per molecule.

Excellent dispersion is possible by using a small amount of the urethane-based dispersant. By making the amount of the dispersant small, the amount of a cure component, etc., can be relatively large. As a result, a color layer with excellent heat resistance can be formed.

In the present invention, the urethane-based dispersant is preferably a reaction product of (1) polyisocyanates having two or more isocyanate groups per molecule and (2) one or more kinds selected from polyesters having a hydroxyl group at a single terminal or both terminals thereof and poly(meth)acrylates having a hydroxyl group at a single terminal or both terminals thereof. The urethane-based dispersant is more preferably a reaction product of (1) polyisocyanates having two or more isocyanate groups per molecule, (2) one or more kinds selected from polyesters having a hydroxyl group at a single terminal or both terminals thereof and poly(meth)acrylates having a hydroxyl group at a single terminal or both terminals thereof, and (3) a compound having an active hydrogen and a basic or acidic group per molecule.

Examples of commercially-available dispersants include Disperbyk-161, 162, 163, 164, 167, 168, 170, 171, 174, 182, 183, 184 and 185, and BYK-9077 (all manufactured by BYK Japan KK), AJISPER PB711 (manufactured by Ajinomoto Co., Inc.) and EFKA-46, 47 and 48 (manufactured by EFKA CHEMICALS). Of them, Disperbyk-161, 162, 166, 170 and 174 are preferred from the viewpoint of heat resistance, electric reliability and dispersibility.

As the dispersant (B), these dispersants can be used alone or in combination of two or more kinds.

In the color material dispersion liquid of the present invention, from the viewpoint of dispersibility and dispersion stability, the content of the dispersant (B) is generally preferably in a range of 1 to 50% by mass, more preferably in a range of 1 to 20% by mass, with respect to the total amount of the dispersion liquid.

[(C) Solvent]

In the present invention, the solvent (C) can be appropriately selected from solvents which are unreactive with components in the color material dispersion liquid or in the below-described color resin composition and which are able to dissolve or disperse them. Concrete examples thereof include organic solvents such as alcohol-based solvents, ether alcohol-based solvents, ester-based solvents, ketone-based solvents, ether alcohol acetate-based solvents, ether-based solvents, aprotic amide-based solvents, lactone-based solvents, unsaturated hydrocarbon-based solvents and saturated hydrocarbon-based solvents. Of them, ester-based solvents are preferred from the viewpoint of solubility upon dispersion and coating properties.

Examples of preferred ester-based solvents include methyl methoxypropionate, ethyl ethoxypropionate, methoxy ethyl acetate, propylene glycol monomethyl ether acetate, 3-methoxy-3-methyl-1-butyl acetate, 3-methoxybutyl acetate, methoxybutyl acetate, ethoxy ethyl acetate, ethyl cellosolve acetate, dipropylene glycol methyl ether acetate, propylene glycol diacetate, 1,3-butylene glycol diacetate, cyclohexanol acetate, 1,6-hexanediol diacetate, diethylene glycol monoethyl ether acetate, and diethylene glycol monobutyl ether acetate.

Of them, propylene glycol monomethyl ether acetate (PGMEA) is preferably used, from the point of view that it has a low risk to the human body and has fast heat-drying properties although it has low volatility at around room temperature. In this case, there is such an advantage that a special washing step is not needed when switching from a conventional color resin composition using PGMEA.

These solvents can be used alone or in combination of two or more kinds.

The color material dispersion liquid of the present invention is prepared by using the solvent (C) generally in an amount of 50 to 95% by mass, preferably 60 to 85% by mass, with respect to the total amount of the color material dispersion liquid. As the solvent amount decreases, the viscosity increases and the dispersibility decreases. As the solvent amount increases, the color material concentration decreases and may result in a difficulty in achieving a target chromaticity coordinate after preparation of the color resin composition for color filters.

(Other Components)

The color material dispersion liquid of the present invention can further contain a dispersion assisting resin and other components as needed, as long as the effects of the present invention are not impaired.

As the dispersion assisting resin, there may be mentioned an alkali soluble resin for example, which will be mentioned below under "Color resin composition for color filters". The particles of the color material becomes less likely to contact with each other due to steric hindrance by the alkali soluble resin, resulting in stabilization of particle dispersion, and the particle dispersion stabilization effect may be effective in reducing the dispersant.

Other components include a surfactant, which is used to increase wettability, a silane coupling agent, which is used to increase adhesion properties, a defoaming agent, a cissing inhibitor, an antioxidant, an aggregation inhibitor and an ultraviolet absorber, for example.

The color material dispersion liquid of the present invention is used as a preliminarily prepared product for preparing the below-described color resin composition for color filters.

That is, the color material dispersion liquid is a color material dispersion liquid which is preliminarily prepared at a stage prior to preparing the below-described color resin composition and whose "the mass of the color material component in the composition"/"the mass of the solid content other than the color material component in the composition" ratio is high. In particular, this ratio ("the mass of the color material component in the composition"/"the mass of the solid content other than the color material component in the composition" ratio) is generally 1.0 or more. By mixing the color material dispersion liquid with at least a binder component, a color resin composition with excellent dispersibility can be prepared.

[Method for Producing the Color Material Dispersion Liquid]

In the present invention, the method for producing the color material dispersion liquid is needed to be a method which can contain the color material (A), the dispersant (B), the solvent (C) and various kinds of additional components used as needed, and which can homogeneously disperse the color material (A-1) in the solvent by the dispersant. The color material dispersion liquid can be prepared by mixing them with a known mixing means.

The dispersion liquid can be prepared by the following method: the dispersant (B) is mixed with the solvent (C) and stirred to produce a dispersant solution; the dispersant solution is mixed with the color material (A-1) and, as needed, other component; and the mixture is dispersed with a known stirrer or disperser, thereby preparing the dispersion liquid.

As the disperser used for the dispersion treatment, there may be mentioned roller mills such as a two-roller mill and a three-roller mill, ball mills such as a vibrating ball mill, paint conditioners, bead mills such as a continuous disk type bead mill and a continuous annular type bead mill, for example. In the case of using a bead mill, a preferred dispersion condition is that the diameter of the beads used is 0.03 to 2.00 mm, more preferably 0.10 to 1.0 mm.

In particular, a preparatory dispersion is carried out with 2 mm zirconia beads, which is a relatively large bead diameter, and then a main dispersion is further carried out with 0.1 mm zirconia beads, which is a relatively small bead diameter. It is preferable to carry out filtration with a 0.5 to 5.0 μm membrane filter after the dispersion treatment.

2. Color Resin Composition for Color Filters

The color resin composition for color filters according to the present invention includes: (A) a color material, (B) a dispersant, (C) a solvent and (D) a binder component, wherein the color material (A) contains a color material (A-1) in which at least the cation represented by the general formula (I) and the monovalent anion represented by the general formula (II) form a salt.

In the color resin composition for color filters according to the present invention, the above-specified color material (A-1) is used as the color material (A) and is dispersed in the solvent (C); therefore, a high-luminance color layer with excellent heat resistance can be formed, with adjusting the color tone of the color layer to a desired color tone.

The color resin composition contains the color material (A), the dispersant (B), the solvent (C) and the binder component (D), and it can contain other components as needed.

Hereinafter, such a color resin composition for color filters will be described. However, the color material (A), the dispersant (B) and the solvent (C) will not be described below, since they can be the same as those of the above-described color material dispersion liquid of the present invention.

[(D) Binder Component]

To provide film-forming and surface adhesion properties, the color resin composition for color filters contains a binder component. To provide sufficient hardness to coating films, it is preferable that a curable binder component is contained in the color resin composition for color filters. The curable binder component is not particularly limited, and conventionally-known curable binder components that are used to form color layers of color filters can be appropriately used.

As the curable binder component, for example, there may be used one containing a photocurable binder component that contains a photocurable resin, the resin being polymerizable and curable by visible light, ultraviolet or electron beam radiation, etc., or a thermosetting binder component that contains a thermosetting resin, the resin being polymerizable and curable by heating.

No developability is required of the curable binder component, when it is possible to form color layers by attaching the color resin composition for color filters selectively in a pattern onto a substrate, such as the ink-jet method. In this case, there may be used a known thermosetting binder component or photosensitive binder component, appropriately, which are used to form color layers of color filters by the ink-jet method, etc.

As the thermosetting binder, a combination of a compound having two or more thermosetting functional groups per molecule and a curing agent is generally used. In addition, a catalyst which can promote a thermosetting reaction can be added. Examples of thermosetting functional groups include an epoxy group, an oxetanyl group, an isocyanate group and an ethylenically unsaturated bond. As the thermosetting functional groups, epoxy groups are preferably used. Concrete examples of the thermosetting binder component include those mentioned in International Publication No. WO2012/144521.

On the other hand, in the case of using a photolithography process to form color layers, a photosensitive binder component with alkali developability is suitably used.

Hereinafter, photosensitive binder components will be explained. However, the curable binder component used in the present invention is not limited to them. Besides the below-described photosensitive binder components, a thermosetting binder component that is polymerizable and curable by heating, such as epoxy resin, can be further used.

Photosensitive binder components include a positive photosensitive binder component and a negative photosensitive binder component. Examples of positive photosensitive binder components include those containing an alkali soluble resin and an o-quinonediazide group-containing compound, which is a photosensitivity-imparting component.

On the other hand, as the negative photosensitive binder component, those containing at least an alkali soluble resin, a polyfunctional monomer and a photoinitiator, are suitably used.

In the color resin composition for color filters, the negative photosensitive binder component is preferred, from the point of view that a pattern can be easily formed by a photolithography method, using existing processes.

Hereinafter, the alkali soluble resin, the polyfunctional monomer and the photoinitiator, which constitute the negative photosensitive binder component, will be explained in detail.

(Alkali Soluble Resin)

In the present invention, the alkali soluble resin can be appropriately selected, as long as it has an acidic group, functions as a binder resin, and is soluble in developing solutions used for pattern formation, particularly preferably in an alkali developing solution.

In the present invention, the alkali soluble resin is preferably a resin having a carboxyl group as the acidic group. Concrete examples thereof include acrylic copolymers having a carboxyl group and epoxy (meth)acrylate resins having a carboxyl group. Of them, particularly preferred is one having a carboxyl group and, moreover, a photopolymerizable functional group such as an ethylenically unsaturated group in a side chain thereof. This is because the hardness of the cured film thus formed is increased by containing the photopolymerizable functional group. These acrylic copolymers and epoxy (meth)acrylate resins can be used in combination of two or more kinds.

An acrylic copolymer having a carboxyl group is obtained by copolymerizing a carboxyl group-containing ethylenically unsaturated monomer and an ethylenically unsaturated monomer.

The acrylic copolymer having a carboxyl group can further contain a constitutional unit having an aromatic carbon ring. The aromatic carbon ring functions as a component which imparts coatability to the color resin composition for color filters.

The acrylic copolymer having a carboxyl group can further contain a constitutional unit having an ester group. The constitutional unit having an ester group not only functions as a component which inhibits alkali solubility of the color resin composition for color filters, but also functions as a component which increases solubility in solvents and re-solubility in solvents.

Concrete examples of the acrylic copolymer having a carboxyl group include those described in International Publication No. WO2012/144521. In particular, there may be mentioned copolymers obtained from a monomer having no carboxyl group, such as methyl (meth)acrylate and ethyl (meth)acrylate, with one or more selected from (meth)acrylic acid and anhydrides thereof. Also, there may be mentioned polymers obtained by introducing an ethylenically unsaturated bond in the above copolymers by, for example, addition of an ethylenically unsaturated compound having a reactive functional group such as a glycidyl group or hydroxyl group. In the present invention, however, the acrylic copolymer having a carboxyl group is not limited to these examples.

Of these examples, the polymers obtained by introducing an ethylenically unsaturated bond in the above copolymers by, for example, addition of an ethylenically unsaturated compound having a glycidyl group or hydroxyl group, are particularly preferred from the point of view that polymerization with the below-described polyfunctional monomer is possible upon exposure, and stable color filters can be obtained.

The copolymerization ratio of the carboxyl group-containing ethylenically unsaturated monomer in the carboxyl group-containing copolymer is generally 5 to 50% by mass, preferably 10 to 40% by mass. When the copolymerization ratio of the carboxyl group-containing ethylenically unsaturated monomer is less than 5% by mass, the solubility of the coating film thus obtained in alkali developing solutions is decreased, resulting in a difficulty with pattern formation. When the copolymerization ratio exceeds 50% by mass, upon development with an alkali developing solution, a pattern thus formed is likely to come off of the substrate, or roughening of the pattern surface is likely to occur.

The molecular weight of the carboxyl group-containing copolymer is preferably in a range of 1,000 to 500,000, more preferably in a range of 3,000 to 200,000. When the molecular weight is less than 1,000, there may be a remarkable decrease in binder function after curing. When the molecular weight exceeds 500,000, upon development with an alkali developing solution, pattern formation may be difficult.

The epoxy (meth)acrylate resin having a carboxyl group is not particularly limited. As the resin, an epoxy (meth)acrylate compound obtained by reaction of an acid anhydride with a reaction product of an epoxy compound and an unsaturated group-containing monocarboxylic acid, is suitable.

The epoxy compound, the unsaturated group-containing monocarboxylic acid and the acid anhydride can be appropriately selected from known ones. Concrete examples thereof include those described in International Publication No. WO2012/144521. As each of the epoxy compound, the unsaturated group-containing monocarboxylic acid and the acid anhydride, those mentioned above can be used alone or in combination of two or more kinds.

The alkali soluble resin used in the color resin composition for color filters can be one kind of alkali soluble resin or a combination of two or more kinds of alkali soluble resins. The content of the alkali soluble resin is generally in a range of 10 to 1,000 parts by mass, preferably in a range of 20 to 500 parts by mass, with respect to 100 parts by mass of the color material contained in the color resin composition. When the content of the alkali soluble resin is too small, sufficient alkali developability may not be obtained. When the content is too large, the ratio of the color material is relatively small, so that sufficient color density may not be obtained.

(Polyfunctional Monomer)

The polyfunctional monomer used in the color resin composition for color filters is not particularly limited, as long as it is polymerizable with the below-described photoinitiator. As the polyfunctional monomer, a compound having two or more ethylenically unsaturated double bonds is generally used. Preferably, the polyfunctional monomer is a polyfunctional (meth)acrylate having two or more acryloyl or methacryloyl groups.

Such a polyfunctional (meth)acrylate can be appropriately selected from conventionally known ones. Concrete examples thereof include those mentioned in International Publication No. WO2012/144521.

These polyfunctional (meth)acrylates can be used alone or in combination of two or more kinds. When excellent photocurability (high sensitivity) is required of the color resin composition the present invention, the polyfunctional monomer is preferably one having three (trifunctional) or more polymerizable double bonds. Preferred are poly(meth) acrylates of trivalent or higher polyalcohols and dicarboxylic acid-modified products thereof. Concrete examples thereof include trimethylolpropane tri(meth)acrylate, pentaerythritol tri(meth)acrylate and succinic acid-modified products of pentaerythritol tri(meth)acrylate, pentaerythritol tetra(meth)acrylate, dipentaerythritol tetra(meth)acrylate, dipentaerythritol penta(meth)acrylate and succinic acid-modified products of dipentaerythritol penta(meth)acrylate, and dipentaerythritol hexa(meth)acrylate.

The content of the polyfunctional monomer used in the color resin composition for color filters is not particularly limited. It is generally about 5 to 500 parts by mass, preferably in a range of 20 to 300 parts by mass, with respect to 100 parts by mass of the alkali soluble resin. When the content of the polyfunctional monomer is smaller than the range, photocuring may not proceed sufficiently and the color resin composition exposed to light may be dissolved. When the content of the polyfunctional monomer is larger than the range, there may be a decrease in alkali developability.

(Photoinitiator)

The photoinitiator used in the color resin composition for color filters is not particularly limited. As the photoinitiator, conventionally-known various kinds of photoinitiators can be used alone or in combination of two or more kinds. Concrete examples thereof include those mentioned in International Publication No. WO2012/144521.

The content of the photoinitiator used in the color resin composition for color filters is generally about 0.01 to 100 parts by mass, preferably 5 to 60 parts by mass, with respect to 100 parts by mass of the polyfunctional monomer. When the content is smaller than the range, sufficient polymerization reaction may not be caused, so that the hardness of the color layer may not be sufficient. When the content is larger than the range, the content of the color material and so on in the solid content of the color resin composition is relatively small, so that sufficient color density may not be obtained.

<Optionally-Added Compounds>

As needed, the color resin composition for color filters can further contain other color material or various kinds of additives.

(Other Color Material)

Other color material can be added as needed, in order to adjust color tone. For example, it can be selected from conventionally-known pigments and dyes, according to the purpose, and such pigments and dyes can be used alone or in combination of two or more kinds.

As the other color material, it is particularly preferable to use the color material described in International Publication No. WO 2012/144521, which contains the divalent or higher cation represented by the general formula (I) and a divalent or higher anion.

Concrete examples of the other color material include pigments such as C. I. Pigment Violet 1, C. I. Pigment Violet 2, C. I. Pigment Violet 3, C. I. Pigment Violet 19, C. I. Pigment Violet 23, C. I. Pigment Blue 1, C. I. Pigment Blue 15, C. I. Pigment Blue 15:3, C. I. Pigment Blue 15:4, C. I. Pigment Blue 15:6, C. I. Pigment Blue 60, C. I. Pigment Red 81, C. I. Pigment Red 82, and dyes such as Acid Red.

In the case of using the other color material, the content is not particularly limited. Especially in the case of using the color material described in International Publication No. WO 2012/144521 as the other material, which contains the divalent or higher cation represented by the general formula (I) and a divalent or higher anion, the color material can be preferably used in a desired amount.

The content of the other color material is preferably 40 parts by mass or less, more preferably 20 parts by mass or less, with respect to 100 parts by mass of the total amount of the color materials. This is because when the content is in this range, color tone can be adjusted without impairing the properties of the color material (A-1), such as high transmittance, heat resistance and light resistance.

(Antioxidant)

From the viewpoint of heat resistance and light resistance, it is preferable that the color resin composition for color filters further contains an antioxidant. The antioxidant can be appropriately selected from conventionally-known ones. Concrete examples of the antioxidant include a hindered phenol-based antioxidant, an amine-based antioxidant, a phosphorus-based antioxidant, a sulfur-based antioxidant and a hydrazine-based antioxidant. From the viewpoint of heat resistance, it is preferable to use a hindered phenol-based antioxidant.

The hindered phenol-based antioxidant means an antioxidant that contains at least one phenol structure in which at least one of the 2- and 6-positions of the hydroxyl group is substituted with a substituent group having 4 or more carbon atoms.

In the case of using the antioxidant, the amount is not particularly limited, as long as it is in a range that does not impair the effects of the present invention. The amount of the antioxidant used is preferably 0.1 to 5.0 parts by mass, more preferably 0.5 to 4.0 parts by mass, with respect to the total solid content 100 parts by mass of the color resin composition. When the amount of the antioxidant used is equal to or more than the lower limit, excellent heat resistance is obtained. When the amount is equal to or less than the upper limit, the color resin composition can be a highly-sensitive photosensitive resin composition.

(Other Additives)

Examples of additives include, besides the above-mentioned antioxidant, a polymerization terminator, a chain transfer agent, a leveling agent, a plasticizer, a surfactant, a defoaming agent, a silane coupling agent, an ultraviolet absorber and an adhesion enhancing agent.

Concrete examples of the surfactant and the plasticizer include those mentioned in International Publication No. WO2012/144521.

<The Content of Each Component in the Color Resin Composition>

The total content of the color material (A) is preferably 3 to 65% by mass, more preferably 4 to 55% by mass, with respect to the total solid content of the color resin composition. When the total content is equal to or more than the lower limit, the color layer obtained by applying the color resin composition for color filters to a predetermined thickness (generally 1.0 to 5.0 μm) has sufficient color density. When the total content is equal to or less than the upper limit, excellent dispersibility and dispersion stability can be obtained, and a color layer with sufficient hardness and adhesion to the substrate can be obtained. In the present invention, "solid content" includes all the above-described components other than the solvent, and it also includes the polyfunctional monomer in a liquid form.

Also, the content of the dispersant (B) is not particularly limited, as long as it is able to homogeneously disperse the color material (A). For example, the dispersant content is 3 to 40 parts by mass, with respect to the total solid content of the color resin composition. More preferably, the content is 5 to 35 parts by mass, particularly preferably 5 to 25 parts by mass, with respect to the total solid content of the color resin composition. When the content is equal to or more than the lower limit, the color material (A) has excellent dispersibility and dispersion stability, and it has excellent storage stability. When the content is equal to or less than the upper limit, excellent developing properties can be obtained.

The total amount of the binder component (D) is 10 to 92% by mass, preferably 15 to 87% by mass, with respect to the total solid content of the color resin composition. When the total amount is equal to or more than the lower limit, a color layer with sufficient hardness and adhesion to the substrate can be obtained. When the total amount is equal to or less than the upper limit, excellent developing properties can be obtained, and generation of fine wrinkles can be inhibited, which is due to heat shrinkage.

The content of the solvent (C) can be appropriately determined in a range which can form a color layer with accuracy. In general, the content is preferably in a range of 55 to 95% by mass, particularly preferably in a range of 65 to 88% by mass, with respect to the total amount of the color resin composition including the solvent. When the content of the solvent is in the range, excellent coatability can be provided to the color resin composition.

<Method for Producing the Color Resin Composition for Color Filters>

The method for producing the color resin composition for color filters is not particularly limited, as long as it is a method in which the color material (A), the dispersant (B), the solvent (C), the binder component (D) and various kinds of additional components that are added as needed are contained, and the color material (A) can be homogeneously dispersed in the solvent (C) by the dispersant (B). The color resin composition can be prepared by mixing them using a known mixing means.

Examples of the method for preparing the color resin composition include the following:

(1) a method of mixing the color material dispersion liquid of the present invention with the binder component (D) and various kinds of additional components used as needed;

(2) a method of adding the color material (A), the dispersant (B), the binder component (D) and various kinds of additional components used as needed to the solvent (C) at the same time and mixing them; and (3) a method of adding the dispersant (B), the binder component (D) and various kinds of additional components used as needed to the solvent (C), mixing them, adding the color material (A) thereto and then mixing them.

Of these methods, the method (1) is preferred, from the viewpoint of effectively preventing the aggregation of the color material and homogeneously dispersing the color material.

3. Color Filter

The color filter according to the present invention includes at least a transparent substrate and color layers disposed on the substrate, wherein at least one of the color layers contains a color material (A-1) in which at least a cation represented by the following general formula (I) and a monovalent anion represented by the following general formula (II) form a salt:

General Formula (I)

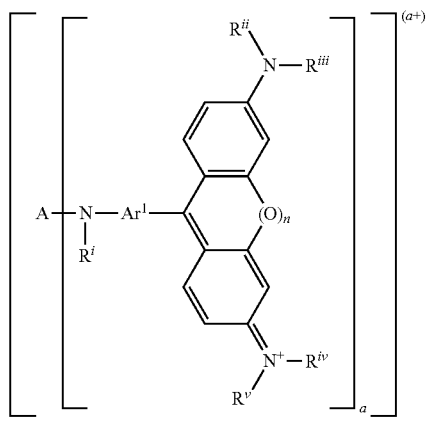

General Formula (II)

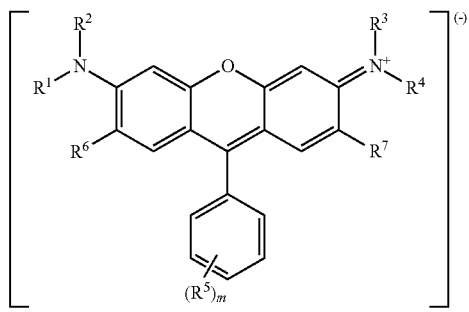

(Symbols in the general formulae (I) and (II) are as described above.)

Such a color filter of the present invention will be explained, with reference to figures. FIG. 1 is a schematic sectional view of an example of the color filter of the present invention. FIG. 1 shows that a color filter 10 of the present invention contains a transparent substrate 1, a light shielding part 2 and a color layer 3.

(Color Layer)

At least one of the color layers used in the color filter of the present invention is a color layer that contains the color material (A-1) in which at least the cation represented by the general formula (I) and the monovalent anion represented by the general formula (II) form a salt.

It is generally formed on an opening of the light shielding part on the below-described transparent substrate and is generally composed of color patterns in three or more colors.

The arrangement of the color layers is not particularly limited and can be a general arrangement such as a stripe type, a mosaic type, a triangle type or a four-pixel arrangement type. The width, area, etc., of the color layer can be determined appropriately.

The thickness of the color layer is appropriately controlled by controlling the applying method, the solid content concentration, viscosity, etc., of the color resin composition for color filters. In general, the thickness is preferably in a range of 1 to 5 μm.

For example, when the color resin composition for color filters is a photosensitive resin composition, the color layer can be formed by the following method. It is preferable that the color layer which is used in the color filter of the present invention and contains the color material (A-1) in which at least the cation represented by the general formula (I) and the monovalent anion represented by the general formula (II) form a salt, is formed using the above-described color resin composition for color filters, which contains: the color material (A), the dispersant (B), the solvent (C) and the binder component (D), wherein the color material (A) contains the color material (A-1) in which at least the cation represented by the general formula (I) and the monovalent anion represented by the general formula (II) form a salt. It is also preferable that the color layer is a cured product of the color resin composition for color filters.

First, the color resin composition for color filters is applied onto the below-described transparent substrate by a coating method such as a spray coating method, a dip coating method, a bar coating method, a roll coating method or a spin coating method to form a wet coating film.

Then, the wet coating film is dried with a hot plate, an oven, etc. The dried film is subjected to exposure through a mask with a given pattern to cause a photopolymerization reaction of the alkali soluble resin, the polyfunctional monomer, etc., thereby obtaining a photosensitive coating film. Examples of light sources and lights that can be used for the exposure include a low pressure mercury lamp, a high pressure mercury lamp and a metal halide lamp, and ultraviolet rays and electron beams. The exposure amount is appropriately controlled, according to the used light source and the thickness of the coating film.

The film can be heated to promote polymerization reaction after the exposure. The heating condition is appropriately determined, depending on the content ratio of the components used in the color resin composition of the present invention, the thickness of the coating film, etc.

Next, the thus-obtained film is developed with a developing solution to dissolve and remove unexposed portions, thereby forming a coating film in a desired pattern. As the developing solution, a solution obtained by dissolving alkali in water or aqueous solvent, is generally used. An appropriate amount of surfactant, etc., can be added to the alkali solution. The developing method can be selected from general developing methods.

After the developing treatment, generally, the developing solution is rinsed off, followed by drying of the cured coating film of the color resin composition, thereby forming a color layer. A heating treatment can be carried out after the developing treatment to sufficiently cure the coating film. The heating condition is not particularly limited and is appropriately determined depending on the intended use of the coating film.

(Light Shielding Part)

In the color filter of the present invention, the light shielding part is formed in pattern on the below-described transparent substrate, and it can be the same as those used in general color filters.

The pattern shape of the light shielding part is not particularly limited, and examples thereof include a stripe-shaped pattern, a matrix-shaped pattern, etc. As the light shielding part, for example, there may be mentioned one produced by dispersing or dissolving a black pigment in a binder resin, and thin metal layers of chromium, chromium oxide, etc. When the light shielding part is such a thin metal layer, the layer can be a stack of two layers of one $CrO_x$ layer (x is an arbitrary number) and one Cr layer, or can be a stack of three layers of one $CrO_x$ layer (x is an arbitrary number), one $CrN_y$ layer (y is an arbitrary number) and one Cr layer, the stack of three layers having a further reduced reflectance.

When the light shielding part is one produced by dispersing or dissolving a black color material in a binder resin, the method for producing the light shielding part is not particularly limited and is only required to be a method which can pattern the light shielding part. For example, there may be mentioned a photolithography method using a color resin composition for the light shielding part, a printing method using the same, an ink-jet method using the same, etc.

When the light shielding part is a thin metal layer, the thickness is about 0.2 to 0.4 μm. When the light shielding part is formed from the black color material dispersed or dissolved in the binder resin, the thickness is about 0.5 to 2 μm.

(Transparent Substrate)

The transparent substrate of the color filter of the present invention is not particularly limited, as long as it is a substrate that is transparent to visible light. It can be selected from general transparent substrates used in color filters. Concrete examples thereof include inflexible transparent rigid materials such as silica glass plate, non-alkali glass plate and synthetic silica plate, and transparent flexible materials with flexibility and flexible properties such as transparent resin film, optical resin plate and flexible glass.

The thickness of the transparent substrate is not particularly limited. Depending on the intended use of the color filter of the present invention, one having a thickness of about 100 μm to 1 mm can be used, for example.

In addition to the transparent substrate, the light shielding part and the color layer, the color filter of the present invention can also contain an overcoat layer and a transparent electrode layer, for example. Moreover, an orientation layer and a columnar spacer can be formed in the color layer.

5. Liquid Crystal Display Device

The liquid crystal display device of the present invention contains the above-described color filter of the present invention, a counter substrate, and a liquid crystal layer disposed between the color filter and the counter substrate.

Figure 2:
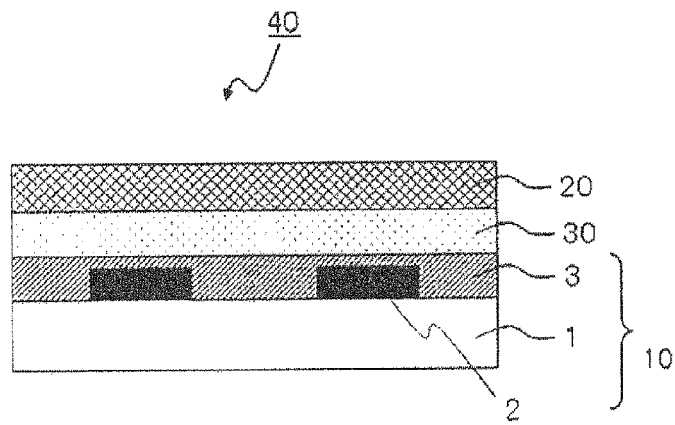
FIG. 2 is a schematic sectional view of an example of the liquid crystal display device of the present invention.

Such a liquid crystal display device of the present invention will be explained with reference to a figure. FIG. 2 is a schematic view of an example of the liquid crystal display device of the present invention. As shown in FIG. 2, a liquid crystal display device 40, which is the liquid crystal display device of the present invention, contains a color filter 10, a counter substrate 20 containing a TFT array substrate, etc., and a liquid crystal layer 30 formed between the color filter 10 and the counter substrate 20.

The liquid crystal display device of the present invention is not limited to the configuration shown in FIG. 2. It can be a configuration which is generally known as a liquid crystal display device containing a color filter.

The method for driving the liquid crystal display device of the present invention is not particularly limited and can be selected from driving methods which are generally used in liquid crystal display devices. Examples of such driving methods include a TN method, an IPS method, an OCB method and an MVA method. In the present invention, any of these methods can be suitably used.

The counter substrate can be appropriately selected, depending on the driving method, etc., of the liquid crystal display device of the present invention.

Also, the liquid crystal constituting the liquid crystal layer can be selected from various liquid crystals with varying dielectric anisotropies and mixtures thereof, depending on the driving method, etc., of the liquid crystal display device of the present invention.

The method for forming the liquid crystal layer can be selected from methods which are generally used to produce liquid crystal cells. Examples thereof include a vacuum injection method and a liquid crystal dripping method.

In the vacuum injection method, for example, a liquid crystal cell is produced in advance, using a color filter and a counter substrate; liquid crystal is heated to become isotropic liquid; the liquid crystal is injected into the liquid crystal cell, in the form of isotropic liquid, using the capillary effect; the liquid crystal cell is encapsulated with an adhesive agent, thereby forming a liquid crystal layer; then, the encapsulated liquid crystal can be oriented by gradually cooling the liquid crystal cell to room temperature.

In the liquid crystal dripping method, for example, a sealing agent is applied to the periphery of the color filter; the color filter is heated to the temperature at which the liquid crystal is in an isotropic phase; the liquid crystal is dripped with a dispenser or the like, in the form of isotropic liquid; the color filter and the counter substrate are stacked under reduced pressure and attached to each other via the applied sealing agent, thereby forming a liquid crystal layer; then, the encapsulated liquid crystal can be oriented by gradually cooling the liquid crystal cell to room temperature.

6. Organic Light-Emitting Display Device

The organic light-emitting display device of the present invention contains the above-described color filter of the present invention and an organic light-emitting material.

Figure 3:
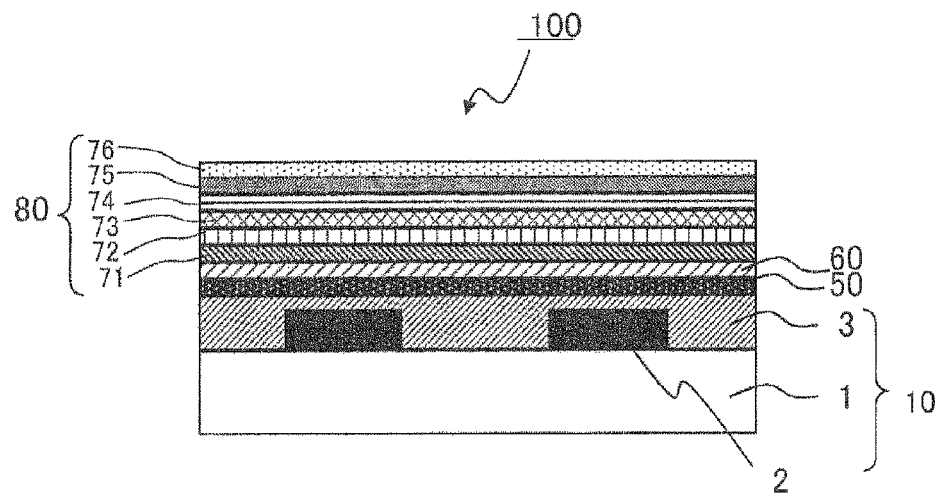
FIG. 3 is a schematic sectional view of an example of the organic light-emitting display device of the present invention.

Such an organic light-emitting display device of the present invention will be explained with reference to a figure. FIG. 3 is a schematic view of an example of the organic light-emitting display device of the present invention. As shown in FIG. 3, an organic light-emitting display device 100, which is the organic light-emitting display device of the present invention, contains a color filter 10 and an organic light-emitting material 80. An organic protection layer 50 and/or an inorganic oxide layer can be disposed between the color filter 10 and the organic light-emitting material 80.

As the method for stacking the components of the organic light-emitting material 80, for example, there may be mentioned a method of stacking a transparent positive electrode 71, a positive hole injection layer 72, a positive hole transport layer 73, a light-emitting layer 74, an electron injection layer 75 and a negative electrode 76 in this sequence on the color filter, a method of attaching the organic light-emitting material 80 formed on a different substrate onto the inorganic oxide layer 60. In the organic light-emitting material 80, the transparent positive electrode 71, the positive hole injection layer 72, the positive hole transport layer 73, the light-emitting layer 74, the electron injection layer 75, the negative electrode 76 and other components can be selected from conventionally-known materials and used. The organic light-emitting display device 100 produced as above is applicable to passive or active drive organic EL displays, for example.

The organic light-emitting display device of the present invention is not limited to the configuration shown in FIG. 3. It can have any one of configurations which are generally known as those of organic light-emitting display devices containing a color filter.

EXAMPLES

Hereinafter, the present invention will be described in detail, by way of examples. The present invention is not limited by these examples.

Synthesis Example 1

Synthesis of Dimeric Triarylmethane Dye

With reference to the method for producing intermediates 3 and 4 described in International Publication No. WO2012/144521, 15.9 g of a dimeric triarylmethane dye represented by the following chemical formula (1) was obtained (yield 70%).

The compound thus obtained was confirmed to be a target compound from the following analysis results:

MS (ESI) (m/z): 511 (+), divalent

Elemental analysis values: CHN measurement values (78.13%, 7.48%, 7.78%); theoretical values (78.06%, 7.75%, 7.69%)

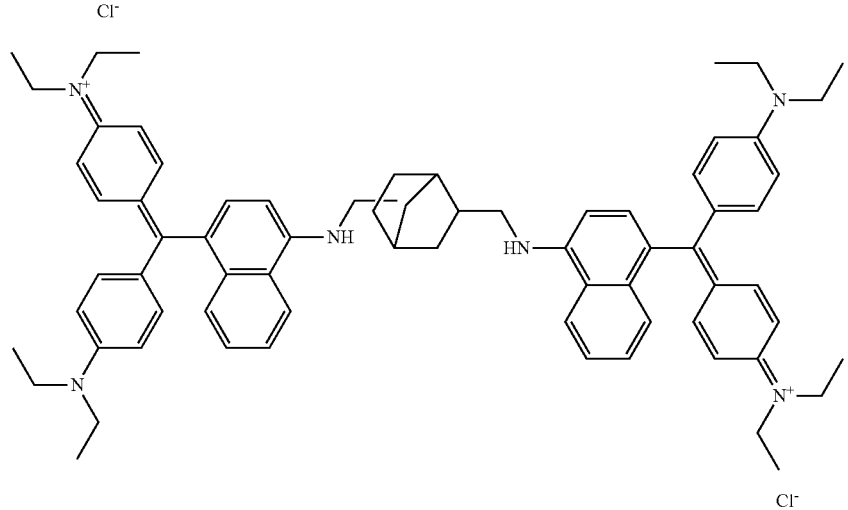

Chemical Formula (1)

Synthesis Example 2

Synthesis of Co-Lake Color Material A1

First, 5 g (4.58 mmol) of the dimeric triarylmethane dye obtained in Synthesis Example 1, which is a basic dye, was added to 300 ml of water and dissolved at 90° C. to prepare a basic dye aqueous solution. Then, 0.620 g (0.916 mmol) of Acid Red 289 (AR289, manufactured by Tokyo Chemical Industry Co., Ltd.), which is an acidic dye, and 9.39 g (2.75 mmol) of phosphotungstic acid n-hydrate $H_3[PW_{12}O_{40}]\cdot nH_2O$ (n=30) (manufactured by Nippon Inorganic Colour & Chemical Co., Ltd.), which is a polyoxometalate, were added to 100 mL of water, and the mixture was stirred at 90° C., thereby preparing an aqueous solution. The aqueous solution thus prepared was added to the basic dye aqueous solution in a dropwise manner for 15 minutes at 90° C., and the mixture was stirred at 90° C. for 1 hour. A precipitate thus produced was obtained by filtration and washed with water. A cake thus obtained was dried to obtain 12.96 g of a co-lake color material A1 represented by the following chemical formula (2) (yield 98%). The co-lake color material A1 corresponds to the color material (A-1) used in the present invention.

Chemical Formula (2)

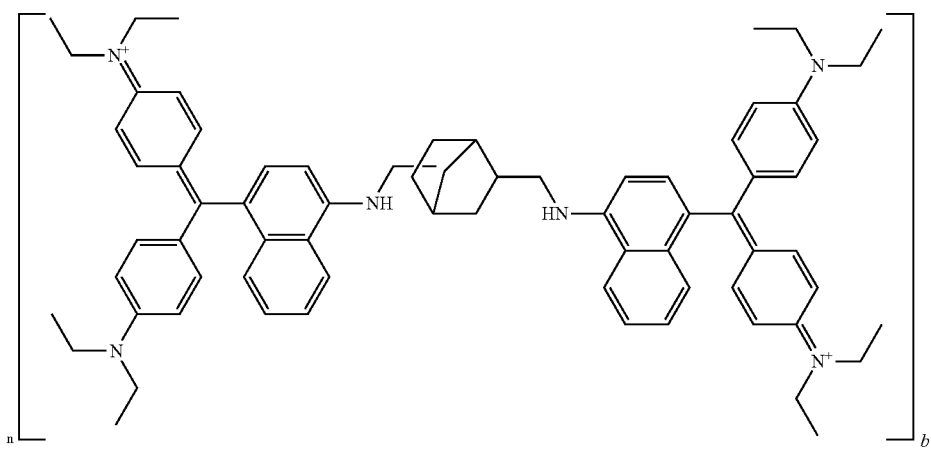

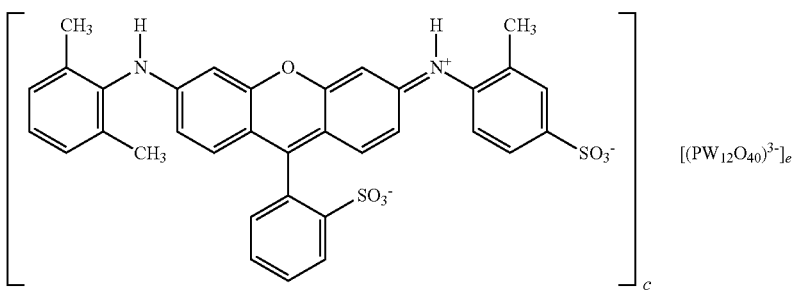

Synthesis Examples 3 to 10

Co-lake color materials A2 to A4, blue lake color materials A1 to A3, and violet lake color materials A1 and A2 were obtained in the same manner as Synthesis Example 2, except that the basic dye, acidic dye and polyoxometalate were changed as shown in Table 1. The co-lake color materials A2 to A4 and the violet lake color material A1 correspond to the color material (A-1) used in the present invention.

In Table 1, the value of each component represents the mass (g) and is expressed as the amount of substance (mmol) in parentheses.

Also, c:(d×e) represents {negative charge derived from acidic dye component negative charge derived from polyoxometalate} in each color material and is 10:90 for the co-lake color material A1, 10:90 for the co-lake color material A2, 30:70 for the co-lake color material A3, and 20:80 for the co-lake color material A4.

TABLE 1

| Synthesis Example | Color material | Basic dye Dimeric triarylmethane dye | Basic Blue 7 | Acidic dye Acid Red 289 | Acid Red 52 | Polyoxometalate Phosphotungstic acid n-hydrate (n = 30) | Phosphomolybdic acid n-hydrate (n = 30) | W:Mo ratio | Yield (%) |
|---|---|---|---|---|---|---|---|---|---|
| Synthesis Example 2 | Co-lake color material A1 | 5.00 (4.58 mmol) | — | 0.620 (0.916 mmol) | — | 9.39 (2.75 mmol) | — | 100:0 | 98 |
| Synthesis Example 3 | Co-lake color material A2 | 5.00 (4.58 mmol) | — | 0.620 (0.916 mmol) | — | 9.21 (2.69 mmol) | 0.130 (0.055 mmol) | 98:2 | 97 |
| Synthesis Example 4 | Co-lake color material A3 | 5.00 (4.58 mmol) | — | 1.86 (2.78 mmol) | — | 7.31 (2.14 mmol) | — | 100:0 | 96 |
| Synthesis Example 5 | Co-lake color material A4 | 5.00 (4.58 mmol) | — | — | 1.06 (1.83 mmol) | 8.35 (2.44 mmol) | — | 100:0 | 95 |
| Synthesis Example 6 | Blue lake color material A1 | 5.00 (4.58 mmol) | — | — | — | 10.44 (3.05 mmol) | — | 100:0 | 99 |
| Synthesis Example 7 | Blue lake color material A2 | 5.00 (4.58 mmol) | — | — | — | 10.23 (2.99 mmol) | 0.144 (0.061 mmol) | 98:2 | 98 |
| Synthesis Example 8 | Blue lake color material A3 | — | 5.00 (9.72 mmol) | — | — | 11.09 (3.24 mmol) | — | 100:0 | 94 |
| Synthesis Example 9 | Violet lake color material A1 | 5.00 (4.58 mmol) | — | 6.20 (9.15 mmol) | — | — | — | — | 81 |
| Synthesis Example 10 | Violet lake color material A2 | — | 5.00 (9.72 mmol) | 6.58 (9.72 mmol) | — | — | — | — | 80 |

Synthesis Example 11

Synthesis of Red Lake Color Material A1

First, 5 g (10.44 mmol) of Rhodamine 6G (manufactured by Taoka Chemical Co., Ltd.), which is a basic dye, was added to 300 ml of water and dissolved at 90° C. to prepare a basic dye aqueous solution. Then, 11.90 g (3.48 mmol) of phosphotungstic acid n-hydrate $H_3[PW_{12}O_{40}]\cdot nH_2O$ (n=30) (manufactured by Nippon Inorganic Colour & Chemical Co., Ltd.), which is a polyoxometalate, was added to 100 mL of water, and the mixture was stirred at 90° C., thereby preparing an aqueous solution. The aqueous solution thus prepared was added to the basic dye aqueous solution in a dropwise manner for 15 minutes at 90° C., and the mixture was stirred at 90° C. for 1 hour. A precipitate thus produced was obtained by filtration and washed with water. A cake thus prepared was dried to obtain 13.25 g of a red lake color material A1 represented by the following chemical formula (3) (yield 96%):

Chemical Formula (3)

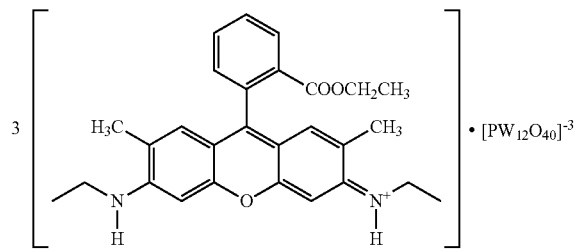

Synthesis Example 12

Synthesis of Binder Resin A

First, 130 parts by mass of diethylene glycol ethyl methyl ether (EMDG), which is a solvent, was put in a reactor equipped with a cooling tube, an addition funnel, a nitrogen inlet, a mechanical stirrer and a digital thermometer. After the temperature of the solvent was increased to 110° C. under a nitrogen atmosphere, a mixture of 32 parts by mass of methyl methacrylate, 22 parts by mass of cyclohexyl methacrylate, 24 parts by mass of methacrylic acid, and 2 parts by mass of α,α'-azobisisobutyronitrile (AIBN), which is an initiator, and 4.5 parts by mass of n-dodecyl mercaptan, which is a chain transfer agent, were continuously added to the solvent in a dropwise manner for 1.5 hours each.

Then, with maintaining the synthesis temperature, the reaction was continued. Two hours after the completion of the addition of the mixture in a dropwise manner, 0.05 part by mass of p-methoxyphenol, which is a polymerization terminator, was added thereto.

Next, with injecting air into the mixture, 22 parts by mass of glycidyl methacrylate was added to the mixture. After the temperature of the mixture was increased to 110° C., 0.2 part by mass of triethylamine was added thereto, and an addition reaction was caused at 110° C. for 15 hours in the mixture, thereby obtaining the binder resin A (solid content 44% by mass).

The binder resin A thus obtained had a mass average molecular weight Mw of 8,500 and an acid value of 85 mgKOH/g. The mass average molecular weight Mw was calculated by gel permeation chromatography (GPC) using polystyrene as a standard material and THF as an eluent. The acid value was measured according to JIS-K0070.

Synthesis Example 13

Synthesis of Organic Phosphonate Ester Compound 1

First, 142.61 parts by mass of diethylene glycol ethyl methyl ether (EMDG), 50.00 parts by mass of phenylphosphonic acid (product name: PPA; manufactured by: Nissan Chemical Industries, Ltd.) and 0.10 part by mass of p-methoxyphenol were put in a reactor equipped with a cooling tube, an addition funnel, a nitrogen inlet, a mechanical stirrer and a digital thermometer. With stirring the mixture under a nitrogen atmosphere, the temperature of the mixture was increased to 120° C. Then, 44.96 parts by mass of glycidyl methacrylate (GMA) was added to the mixture in a dropwise manner for 30 minutes. The mixture was then heated and stirred for 2 hours, thereby obtaining a 40.0% by mass solution of the organic phosphonate ester compound 1, in which half the divalent acidic groups of the PPA were esterified with the epoxy groups of the GMA. The progress of the esterification reaction was confirmed by an acid value measurement. The composition ratio of the product thus obtained was confirmed by a $^{31}$P-NMR measurement. The acid value was 190 mgKOH/g. The composition ratio was as follows: the organic phosphonate monoester compound was 55% by mass; the organic phosphonate diester compound was 23% by mass; and the PPA was 22% by mass.

Synthesis Example 14

Preparation of Phosphate-Modified Dispersant Solution A

In a 100 mL recovery flask, 30.07 parts by mass of PGMEA and 10.15 parts by mass (active solid content 6.09 parts by mass) of a block copolymer containing tertiary amino groups (a block copolymer having a constitutional unit represented by the general formula (IV) and a constitutional unit represented by the general formula (V)) (product name: BYK-LPN 6919; manufactured by: BYK-Chemie GmbH) (amine value 120 mgKOH/g, solid content 60% by mass) were dissolved. Then, 9.78 parts by mass (active solid content 3.91 parts by mass) (1.0 molar equivalent with respect to the tertiary amino groups of the block copolymer) of the organic phosphonate ester compound 1 of Synthesis Example 13 was added to the mixture. The mixture was stirred at 40° C. for 30 minutes, thereby preparing the phosphate-modified dispersant solution A (solid content 20% by mass). At this time, the amino groups of the block copolymer included those forming salts by an acid-base reaction with the acidic groups of the organic phosphonate ester compound 1.

Synthesis Example 15

Preparation of Phosphate-Modified Dispersant Solution B

In a 100 mL recovery flask, 34.30 parts by mass of PGMEA and 14.26 parts by mass (active solid content 8.55 parts by mass) of BYK-LPN 6919 were dissolved. Then, 1.45 parts by mass (0.5 molar equivalent with respect to the tertiary amino groups of the block copolymer) of phenylphosphonic acid (product name: PPA; manufactured by: Nissan Chemical Industries, Ltd.) was added to the mixture. The mixture was stirred at 40° C. for 30 minutes, thereby preparing the phosphate-modified dispersant solution B (solid content 20% by mass). At this time, the amino groups of the block copolymer included those forming salts by an acid-base reaction with the acidic groups of the PPA.

Synthesis Example 16

Production of Graft Polymer A

<Production of Macromonomer A>

First, 80.0 parts by mass of propylene glycol monomethyl ether acetate (PGMEA) was put in a reactor equipped with a cooling tube, an addition funnel, a nitrogen inlet, a mechanical stirrer and a digital thermometer. With stirring under a nitrogen flow, the temperature of the PGMEA was increased to 90° C. Then, a mixed solution of 50.0 parts by mass of methyl methacrylate, 15.0 parts by mass of n-butyl methacrylate, 15.0 parts by mass of benzyl methacrylate, 20.0 parts by mass of 2-ethoxyethyl methacrylate, 4.0 parts by mass of mercaptoethanol, 30 parts by mass of PGMEA, and 1.0 part by mass of α,α'-azobisisobutyronitrile (AIBN) was added to the PGMEA in a dropwise manner for 1.5 hours, and the mixture was reacted for 3 hours. Next, the nitrogen flow was stopped, and the reaction solution was cooled to 80° C. Then, 8.74 parts by mass of Karenz MOI (manufactured by Showa Denko K. K.), 0.125 part by mass of dibutyltin dilaurate, 0.125 part by mass of p-methoxyphenol, and 10 parts by mass of PGMEA were added to the reaction solution, and the reaction solution was stirred for 3 hours, thereby obtaining a 49.5% by mass solution of the macromonomer A. The macromonomer A thus obtained was confirmed by gel permeation chromatography (GPC) in a condition of N-methylpyrrolidone, addition of 0.01 mol/L lithium bromide/polystyrene standard. As a result, the macromonomer A had a mass average molecular weight (Mw) of 4,040, a number average molecular weight (Mn) of 1,930 and a molecular weight distribution (Mw/Mn) of 2.09.
<Synthesis of Graft Copolymer A>

First, 80.0 parts by mass of PGMEA was put in a reactor equipped with a cooling tube, an addition funnel, a nitrogen inlet, a mechanical stirrer and a digital thermometer. With stirring under a nitrogen flow, the temperature of the PGMEA was increased to 85° C. Then, a mixed solution of 67.33 parts by mass (active solid content 33.33 parts by mass) of the macromonomer A solution, 16.67 parts by mass of 2-(dimethylamino)ethyl methacrylate (DMA), 1.24 parts by mass of n-dodecyl mercaptan, 20.0 parts by mass of PGMEA, and 0.5 part by mass of AIBN, was added in a dropwise manner for 1.5 hours. The mixture was then heated and stirred for 3 hours. A mixed solution of 0.10 part by mass of AIBN and 10.0 parts by mass of PGMEA was added thereto in a dropwise manner for 10 minutes. The mixture was further heated at the same temperature for 1 hour, thereby obtaining a 26.0% by mass solution of the graft copolymer A. As a result of GPC measurement, the thus-obtained graft copolymer A had a mass average molecular weight (Mw) of 11,510, a number average molecular weight (Mn) of 4,730, and a molecular weight distribution (Mw/Mn) of 2.43.

Synthesis Example 17

Preparation of Phosphate-Modified Dispersant Solution C

In a 100 mL recovery flask, 16.77 parts by mass of PGMEA and 23.50 parts by mass (active solid content 6.11 parts by mass) of the graft copolymer A of Synthesis Example 16 (a graft copolymer having a constitutional unit represented by the general formula (IV) and a constitutional unit represented by the general formula (VI)) were dissolved. Then, 9.72 parts by mass (active solid content 3.89 parts by mass) (1.0 molar equivalent with respect to the tertiary amino groups of the graft copolymer) of the organic phosphonate ester compound 1 of Synthesis Example 13 was added to the mixture. The mixture was stirred at 40° C. for 30 minutes, thereby preparing the phosphate-modified dispersant solution C (solid content 20% by mass). At this time, the amino groups of the graft copolymer included those forming salts by an acid-base reaction with the acidic groups of the organic phosphonate ester compound 1.

Production Example 1

Preparation of Color Material Dispersion Liquid A

First, 13.0 parts by mass of the co-lake color material A1 prepared in Synthesis Example 2, which is a color material, 22.75 parts by mass (active solid content 4.55 parts by mass) of the phosphate-modified dispersant solution A prepared in Synthesis Example 14, 13.30 parts by mass (active solid content 5.85 parts by mass) of the binder resin A of Synthesis Example 12, and 50.95 parts by mass of PGMEA were mixed. Using a paint shaker (manufactured by Asada Iron Works Co., Ltd.), the mixture was subjected to a pre-dispersion for 1 hour with 2 mm zirconia beads and then a main dispersion for 4 hours with 0.1 mm zirconia beads, thereby obtain the color material dispersion liquid A.

Production Examples 2 to 11

Preparation of Color Material Dispersion Liquids B to K

The color material dispersion liquids B to K were prepared in the same manner as Production Example 1, except that the color material and the dispersion time were changed as shown in Table 2.

TABLE 2

| Production Example | Color material dispersion liquid | Color material content (part by mass) | | Dispersion time (hr) |
|---|---|---|---|---|---|
| | | Blue color material | | Violet color material | |
| Production Example 1 | Color material dispersion liquid A | Co-lake color material A1 | 13 | — | — | 4 |
| Production Example 2 | Color material dispersion liquid B | Co-lake color material A2 | 13 | — | — | 4 |
| Production Example 3 | Color material dispersion liquid C | Co-lake color material A3 | 13 | — | — | 4 |
| Production Example 4 | Color material dispersion liquid D | Blue lake color material A1 | 13 | — | — | 4 |

TABLE 2-continued

| Production Example | Color material dispersion liquid | Color material content (part by mass) | | | | Dispersion time (hr) |
|---|---|---|---|---|---|---|
| | | Blue color material | | Violet color material | | |
| Production Example 5 | Color material dispersion liquid E | Blue lake color material A2 | 13 | — | — | 4 |
| Production Example 6 | Color material dispersion liquid F | Blue lake color material A3 | 13 | — | — | 4 |
| Production Example 7 | Color material dispersion liquid G | Copper phthalocyanine pigment | 13 | — | — | 4 |
| Production Example 8 | Color material dispersion liquid H | — | — | Violet lake color material A1 | 13 | 3 |
| Production Example 9 | Color material dispersion liquid I | — | — | Violet lake color material A2 | 13 | 3 |
| Production Example 10 | Color material dispersion liquid J | Blue lake color material A1 | 11.7 | Dioxazine pigment | 1.3 | 4 |
| Production Example 11 | Color material dispersion liquid K | Copper phthalocyanine pigment | 9.75 | Dioxazine pigment | 3.25 | 4 |

In Table 2,
Dioxazine pigment: C. I. Pigment Violet 23 (primary particle diameter 60 nm)
Copper phthalocyanine pigment: C. I. Pigment Blue 15:6 (primary particle diameter 40 nm)

Example 1

First, 28.57 parts by mass of the color material dispersion liquid H obtained in Production Example 8, 28.29 parts by mass of the following binder composition A, 43.14 parts by mass of PGMEA, 0.04 part by mass of surfactant R08MH (manufactured by DIC) and 0.4 part by mass of silane coupling agent KBM503 (manufactured by Shin-Etsu Silicones) were mixed. The mixture thus obtained was subjected to pressure filtration, thereby obtaining a color resin composition A.
<Binder Composition A (Solid Content 40% by Mass)>
  Alkali soluble resin (the binder resin A of Synthesis Example 4, solid content 44% by mass): 18.18 parts by mass
  Pentafunctional to hexafunctional acrylate monomer (product name: ARONIX M403; manufactured by TOAGOSEI Co., Ltd.): 8.00 parts by mass
  Photopolymerization initiator: 2-methyl-1[4-(methylthio)phenyl]-2-morpholinopropane-1-one (product name: Irgacure 907; manufactured by: BASF): 3.00 parts by mass
  Photosensitizer: 2,4diethylthioxanthone (product name: KAYACURE DETX-S; manufactured by: Nippon Kayaku Co., Ltd.): 1.00 part by mass
  Solvent: propylene glycol monomethyl ether acetate (PGMEA): 19.82 parts by mass Examples 2 to 8

Color resin compositions C, E, F, I, J, K and L were obtained in the same manner as Example 1, except that the color material dispersion liquid was changed as shown in Table 3.

Comparative Examples 1 to 6

Color resin compositions B, D, G, H, M and N were obtained in the same manner as Example 1, except that the color material dispersion liquid was changed as shown in Table 3.

TABLE 3

| Example | Color resin composition | Dispersion liquid content (part by mass) | | | |
|---|---|---|---|---|---|
| Example 1 | Color resin composition A | — | — | Color material dispersion liquid H | 28.57 |
| Comparative Example 1 | Color resin composition B | — | — | Color material dispersion liquid I | 28.57 |
| Example 2 | Color resin composition C | Color material dispersion liquid G | 20.00 | Color material dispersion liquid H | 8.57 |
| Comparative Example 2 | Color resin composition D | Color material dispersion liquid G | 20.00 | Color material dispersion liquid I | 8.57 |
| Example 3 | Color resin composition E | Color material dispersion liquid C | 28.57 | — | — |
| Example 4 | Color resin composition F | Color material dispersion liquid D | 20.00 | Color material dispersion liquid H | 8.57 |
| Comparative Example 3 | Color resin composition G | Color material dispersion liquid D | 20.00 | Color material dispersion liquid I | 8.57 |
| Comparative Example 4 | Color resin composition H | Color material dispersion liquid F | 20.00 | Color material dispersion liquid I | 8.57 |
| Example 5 | Color resin composition I | Color material dispersion liquid A | 28.57 | — | — |
| Example 6 | Color resin composition J | Color material dispersion liquid D | 25.71 | Color material dispersion liquid H | 2.86 |
| Example 7 | Color resin composition K | Color material dispersion liquid B | 28.57 | — | — |
| Example 8 | Color resin composition L | Color material dispersion liquid E | 25.71 | Color material dispersion liquid H | 2.86 |

TABLE 3-continued

| Example | Color resin composition | Dispersion liquid content (part by mass) | | |
|---|---|---|---|---|
| Comparative Example 5 | Color resin composition M | Color material dispersion liquid J | 28.57 | — | — |
| Comparative Example 6 | Color resin composition N | Color material dispersion liquid K | 28.57 | — | — |

Comparative Example 7

First, 20.00 parts by mass of the color material dispersion liquid H obtained in Production Example 8, 1.70 parts by mass of a 10% by mass methanol solution of AR289, 30.52 parts by mass of the binder composition A, 47.78 parts by mass of PGMEA, 0.04 part by mass of surfactant R08MH (manufactured by DIC) and 0.4 part by mass of silane coupling agent KBM503 (manufactured by Shin-Etsu Silicones) were mixed. The mixture thus obtained was subjected to pressure filtration, thereby obtaining a color resin composition O.

(Evaluation)
<Optical Performance Evaluation, Heat Resistance Evaluation>

Each of the blue color resin compositions obtained in Examples and Comparative Examples was applied onto a glass substrate having a thickness of 0.7 mm ("OA-10G" manufactured by Nippon Electric Glass Co., Ltd.) using a spin coater, heat-dried on a hot plate at 80° C. for 3 minutes, and then irradiated with ultraviolet light at 40 mJ/cm² using a ultrahigh-pressure mercury lamp, thereby obtaining a cured film (blue color layer). The color substrate was subjected to post-baking (it may be referred to as "PB" in Tables) in a clean oven at 230° C. for 60 minutes. The chromaticity (x, y), luminance (Y) and color coordinates (L, a, b) of the thus-obtained color layer before and after the post-baking, were measured using microscopic spectrophotometer "OSP-SP200" manufactured by Olympus Corporation. The contrast was measured using contrast measuring device "CT-1B" manufactured by Tsubosaka Electric Co., Ltd.

Given that the color coordinates before the post-baking are determined as $L_1$, $a_1$, $b_1$ and the color coordinates after the post-baking are determined as $L_2$, $a_2$, $b_2$, the chromaticity ($\Delta Eab$) is calculated by the following formula and used as an indicator of heat resistance. At this time, when the value of $\Delta Eab$ is 10 or less, the color resin composition is determined to be particularly suitable for practical use. When the value of $\Delta Eab$ is more than 20, the color resin composition is determined to be unsuitable for practical use.

$$\Delta Eab = \{(L_2-L_1)^2 + (a_2-a_1)^2 + (b_2-b_1)^2\}^{1/2}$$

Evaluation results are shown in Tables 4 to 7.

TABLE 4

| Example | Color resin composition | Color material | Optical performance (230° C., 60 min, after PB) | | | | |
|---|---|---|---|---|---|---|---|
| | | | x | y | Y | C/R | ΔEab |
| Example 1 | Color resin composition A | Violet lake color material A1 | 0.1612 | 0.0300 | 2.07 | 2,678 | 14.5 |
| Comparative Example 1 | Color resin composition B | Violet lake color material A2 | 0.1663 | 0.0300 | 1.91 | 713 | 22.8 |

TABLE 5

| Example | Color resin composition | Color material | | Optical performance (230° C., 60 min, after PB) | | | | |
|---|---|---|---|---|---|---|---|---|
| | | | | x | y | Y | C/R | ΔEab |
| Example 2 | Color resin composition C | Copper phthalocyanine pigment | Violet lake color material A1 | 0.1466 | 0.0570 | 5.10 | 2,486 | 12.5 |
| Comparative Example 2 | Color resin composition D | Copper phthalocyanine pigment | Violet lake color material A2 | 0.1469 | 0.0570 | 4.94 | 1,455 | 13.0 |

TABLE 6

| Example | Color resin composition | Color material | | Optical performance (230° C., 60 min, after PB) | | | | |
|---|---|---|---|---|---|---|---|---|
| | | | | x | y | Y | C/R | ΔEab |
| Example 3 | Color resin composition E | Co-lake color material A3 | | 0.1514 | 0.0570 | 5.99 | 3,662 | 6.6 |
| Example 4 | Color resin composition F | Blue lake color material A1 | Violet lake color material A1 | 0.1528 | 0.0570 | 5.85 | 3,914 | 8.8 |
| Comparative Example 3 | Color resin composition G | Blue lake color material A1 | Violet lake color material A2 | 0.1538 | 0.0570 | 5.66 | 2,260 | 9.5 |

TABLE 6-continued

| | Color resin | | | Optical performance (230° C., 60 min, after PB) | | | | |
|---|---|---|---|---|---|---|---|---|
| Example | composition | Color material | | x | y | Y | C/R | ΔEab |
| Comparative Example 4 | Color resin composition H | Blue lake color material A3 | Violet lake color material A2 | 0.1617 | 0.0570 | 5.09 | 1,319 | 34.0 |

TABLE 7

| | Color resin | | | Optical performance (230° C., 60 min, after PB) | | | | |
|---|---|---|---|---|---|---|---|---|
| Example | composition | Color material | | x | y | Y | C/R | ΔEab |
| Example 5 | Color resin composition I | Co-lake color material A1 | | 0.1462 | 0.0820 | 9.71 | 4,048 | 7.6 |
| Example 6 | Color resin composition J | Blue lake color material A1 | Violet lake color material A1 | 0.1470 | 0.0820 | 9.56 | 4,945 | 8.5 |
| Example 7 | Color resin composition K | Co-lake color material A2 | | 0.1469 | 0.0820 | 9.49 | 4,739 | 7.9 |
| Example 8 | Color resin composition L | Blue lake color material A2 | Violet lake color material Al | 0.1478 | 0.0820 | 9.34 | 4,806 | 9.2 |
| Comparative Example 5 | Color resin composition M | Blue lake color material A1 | Dioxazine pigment | 0.1466 | 0.0820 | 9.12 | 3,600 | 8.9 |
| Comparative Example 6 | Color resin composition N | Copper phthalocyanine pigment | Dioxazine pigment | 0.1464 | 0.0820 | 8.72 | 3,090 | 3.1 |
| Comparative Example 7 | Color resin composition O | Blue lake color material A1 | AR289 | Not evaluated due to precipitation | | | | |

[Results]

From the results in Table 4, the color layer formed with the blue color resin composition of Example 1, which contains the violet lake color material A1 in which the cation represented by the general formula (I) and the monovalent anion represented by the general formula (II) form a salt, can be evaluated as a high-luminance color material with high heat resistance, because the color layer is smaller in lEab and higher in luminance than Comparative Example 1 using the color material in which Basic Blue 7 and the monovalent anion represented by the general formula (II) form a salt.

This advantage is also clear from the following: as is shown by a comparison between Example 2 and Comparative Example 2 in Table 5, this advantage is maintained in the case of being combined with the copper phthalocyanine pigment, and as is shown by a comparison between Example 4 and Comparative Example 3 in Table 6, this advantage is also maintained in the case of being combined with the blue lake color material. From these results, it is clear that the color material in which the cation represented by the general formula (I) and the monovalent anion represented by the general formula (II) form a salt, is excellent as a color material for adjusting the color of the blue color material.

Next, from a comparison between Example 6 and Comparative Example 5 in Table 7, Example 6 using the violet lake color material A1 in which the cation represented by the general formula (I) and the monovalent anion represented by the general formula (II) form a salt, is remarkably higher in luminance after the post-baking and is better in heat resistance than Comparative Example 5 using the dioxazine pigment. As is shown by Comparative Example 6, the dioxazine pigment is excellent in heat resistance when combined with other pigment. However, when the dioxazine was combined with the dimeric triarylmethane dye, the heat resistance decreased (Comparative Example 5). From these results, it is clear that in the case of combining the color material in which the cation represented by the general formula (I) and the monovalent anion represented by the general formula (II) form a salt, with the dimeric triarylmethane dye, the effects of high luminance after the post-baking and excellent heat resistance become remarkable.

The color resin composition O of Comparative Example 7 could not be evaluated since particles (which are considered to be AR289) were heavily precipitated after the color resin composition was applied using the spin coater and heat-dried on the hot plate at 80° C. for 3 minutes.

In addition, considering all the results in detail, it is clear from comparisons between Example 3 and Example 4, between Example 5 and Example 6, and between Example 7 and Example 8, that the color layer using the color material represented by the general formula (III), which was obtained by laking the dimeric triarylmethane dye, AR289 and the heteropolyoxometalate at the same time, is particularly small in ΔEab and high in luminance. This is considered to result from the following: the heat resistance of the dyes were further increased by that the dimeric triarylmethane dye, AR289 and the heteropolyoxometalate were laked in such a manner that AR289 was incorporated in the color material having a three-dimensional crosslinking structure composed of the dimeric triarylmethane dye and the heteropolyoxometalate.

Production Example 12

Preparation of Color Material Dispersion Liquid L

First, 13.0 parts by mass of the co-lake color material A1 prepared in Synthesis Example 2, which is a color material, 22.75 parts by mass (active solid content 4.55 parts by mass) of the phosphate-modified dispersant solution B prepared in Synthesis Example 15, 13.30 parts by mass (active solid content 5.85 parts by mass) of the binder resin A of Synthesis Example 12, and 50.95 parts by mass of PGMEA were mixed.

Then, using a paint shaker (manufactured by Asada Iron Works Co., Ltd.), the mixture was subjected to a pre-dispersion for 1 hour with 2 mm zirconia beads and then a main dispersion for 4 hours with 0.1 mm zirconia beads, thereby obtaining the color material dispersion liquid L.

Production Example 13

Preparation of Color Material Dispersion Liquid M

The color material dispersion liquid M was obtained in the same manner as Production Example 12, except that the phosphate-modified dispersant solution C was used in place of the phosphate-modified dispersant solution B.

Production Example 14

Preparation of Color Material Dispersion Liquid N

The color material dispersion liquid N was obtained in the same manner as Production Example 12, except that 15.17 parts by mass of Disperbyk-161 (a urethane-based dispersant manufactured by BYK-Chemie GmbH, solid content 30% by mass) was used in place of the phosphate-modified dispersant solution B, and the amount of the PGMEA was changed to 58.54 parts by mass.

Production Example 15

Preparation of Color Material Dispersion Liquid O

The color material dispersion liquid O was obtained in the same manner as Production Example 12, except that 11.38 parts by mass of BYK-LPN 21116 (a block copolymer manufactured by BYK-Chemie GmbH, solid content 40% by mass) was used in place of the phosphate-modified dispersant solution B, and the amount of the PGMEA was changed to 62.33 parts by mass.

Production Example 16

Preparation of Color Material Dispersion Liquid P

The color material dispersion liquid P was obtained in the same manner as Production Example 12, except that the co-lake color material A4 of Synthesis Example 5 was used in place of the co-lake color material A1.

Production Example 17

Preparation of Color Material Dispersion Liquid Q

The color material dispersion liquid Q was obtained in the same manner as Production Example 12, except that 11.7 parts by mass of the blue lake color material A1 of Synthesis Example 6 and 1.3 parts by mass of the red lake color material A1 of Synthesis Example 11 were used in place of the co-lake color material A1.

Production Example 18

Preparation of Color Material Dispersion Liquid R

The color material dispersion liquid R was obtained in the same manner as Production Example 12, except that the blue lake color material A1 of Synthesis Example 6 was used in place of the co-lake color material A1.

Production Example 19

Preparation of Color Material Dispersion Liquid S

The color material dispersion liquid S was obtained in the same manner as Production Example 12, except that the blue lake color material A3 of Synthesis Example 8 was used in place of the co-lake color material A1.

Example 9

A color resin composition 1-2 was obtained in the same manner as Example 1, except that the color material dispersion liquid L of Production Example 12 was used in place of the color material dispersion liquid H.

Example 10

A color resin composition I-3 was obtained in the same manner as Example 9, except that the color material dispersion liquid M of Production Example 13 was used in place of the color material dispersion liquid L.

Example 11

A color resin composition 1-4 was obtained in the same manner as Example 9, except that the color material dispersion liquid N of Production Example 14 was used in place of the color material dispersion liquid L.

Example 12

A color resin composition 1-5 was obtained in the same manner as Example 9, except that the color material dispersion liquid O of Production Example 15 was used in place of the color material dispersion liquid L.

Example 13

A color resin composition P was obtained in the same manner as Example 9, except that the color material dispersion liquid P of Production Example 16 was used in place of the color material dispersion liquid L.

Comparative Example 8

A color resin composition Q was obtained in the same manner as Example 9, except that the color material dispersion liquid Q of Production Example 17 was used in place of the color material dispersion liquid L.

Comparative Example 9

A color resin composition R was obtained in the same manner as Example 9, except that the color material dispersion liquid R of Production Example 18 was used in place of the color material dispersion liquid L.

Comparative Example 10

A color resin composition S was obtained in the same manner as Example 9, except that the color material dispersion liquid S of Production Example 19 was used in place of the color material dispersion liquid L.

(Evaluation)

<Optical Performance Evaluation, Heat Resistance Evaluation>

The color resin compositions of Examples 9 to 14 and 5, and those of Comparative Examples 8 to 11 and 5 were evaluated for optical performance and heat resistance, in the same manner as above. The results are shown in Table 8.

<Temporal Stability Evaluation>

The color resin compositions of Examples 9 to 14 and Comparative Examples 8 to 11 were measured for shear viscosity (mPa·sec) at a shear rate of 60 rpm, using "Rheometer MCR301" manufactured by Anton Paar. For evaluation, each color resin composition was measured for the viscosity just after the preparation and the viscosity after 7 days of storage at room temperature. The results are shown in Table 8.

3. Color layer
10. Color filter
20. Counter substrate
30. Liquid crystal layer
40. Liquid crystal display device
50. Organic protection layer
60. Inorganic oxide layer
71. Transparent positive electrode
72. Positive hole injection layer
73. Positive hole transport layer
74. Light-emitting layer
75. Electron injection layer
76. Negative electrode
80. Organic light-emitting material

TABLE 8

| Example | Color resin composition | Color material | | Optical performance (230° C., 60 min, after PB) | | | | | Viscosity | |
|---|---|---|---|---|---|---|---|---|---|---|
| | | | x | y | Y | C/R | ΔEab | Initial | After 7 days |
| Example 5 | Color resin composition I | Co-lake color material A1 | | 0.1462 | 0.0820 | 9.71 | 4,048 | 7.6 | 2.63 | 2.65 |
| Example 9 | Color resin composition I-2 | Co-lake color material A1 | | 0.1462 | 0.0820 | 9.77 | 4,120 | 6.8 | 2.68 | 2.65 |
| Example 10 | Color resin composition I-3 | Co-lake color material A1 | | 0.1460 | 0.0820 | 9.77 | 4,230 | 5.8 | 2.65 | 2.69 |
| Example 11 | Color resin composition I-4 | Co-lake color material A1 | | 0.1455 | 0.0820 | 9.76 | 3,967 | 4.3 | 2.85 | 2.81 |
| Example 12 | Color resin composition I-5 | Co-lake color material A1 | | 0.1467 | 0.0820 | 9.58 | 4,061 | 11.9 | 2.71 | 2.66 |
| Example 13 | Color resin composition P | Co-lake color material A4 | | 0.1445 | 0.0820 | 9.84 | 2,819 | 3.9 | 2.67 | 2.68 |
| Comparative Example 5 | Color resin composition M | Blue lake color material A1 | Dioxazine pigment | 0.1466 | 0.0820 | 9.12 | 3,600 | 8.9 | 2.69 | 5.04 |
| Comparative Example 8 | Color resin composition Q | Blue lake color material A1 | Red lake color material A1 | 0.1480 | 0.0820 | 9.43 | 4,526 | 11.9 | 2.79 | 6.54 |
| Comparative Example 9 | Color resin composition R | Blue lake color material A1 | | 0.1398 | 0.0820 | 9.33 | 4,890 | 7.5 | 2.70 | 5.19 |
| Comparative Example 10 | Color resin composition S | Blue lake color material A3 | | 0.1514 | 0.1464 | 16.83 | 4,718 | 65.6 | 2.64 | 2.65 |

CONCLUSION

As is shown by the results in Table 8, the color resin compositions containing the blue lake color material A1, such as Comparative Examples 5, 8 and 9, showed an increase in viscosity over time. Meanwhile, it is clear that the color resin compositions of Examples 5 and 9 to 13, which were prepared using the co-lake color material A1 or A4 represented by the general formula (III'), are excellent in temporal stability and high in luminance after the post-baking. The color resin composition of Comparative Example 10 was excellent in temporal stability; however, it was very poor in heat resistance, so that the color was severely deteriorated after the post-baking and could not compared in the standard color.

For the substrate to which the color resin composition Q of Comparative Example 8 was applied, it was found that at the time of post-baking, a red dye, which is considered to be derived from the red lake color material A1, attaches to and contaminates the environment. This is considered to be because the red lake color material A1 was sublimated by heat.

REFERENCE SIGNS LIST

1. Transparent substrate
2. Light shielding part
100. Organic light-emitting display device
101. Color-forming moiety
102. Linking group A
103. Cation represented by the general formula (I)
104. Monovalent anion represented by the general formula (II)
105. Polyoxometalate anion
106. Polyoxometalate anion not forming a salt
107. Cation being represented by the general formula (I) and not forming a salt
110. Color material (A-1)
120. Color material represented by the general formula (III)
130. Color material represented by the general formula (III')

The invention claimed is:

1. A color material dispersion liquid comprising: (A) a color material, (B) a dispersant and (C) a solvent, wherein the color material (A) contains a color material (A-1) in which at least a cation represented by the following general formula (I) and a monovalent anion represented by the following general formula (II) form a salt:

General Formula (I)

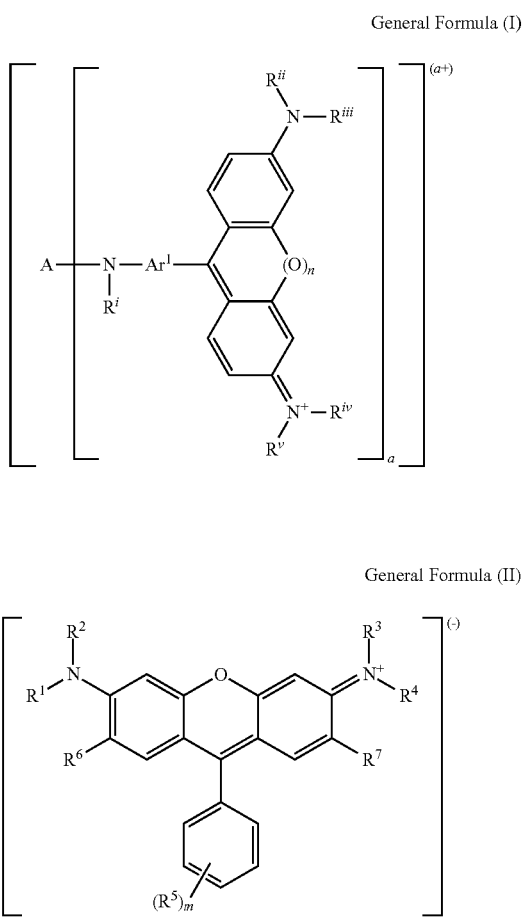

General Formula (II)

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$s can be the same or different; a plurality of $R^v$s can be the same or different; a plurality of $Ar^1$s can be the same or different; "a" is a number of 2 or more; "n" is 0 or 1, and there is no bond when "n" is 0; and a plurality of "n"s can be the same or different; and wherein each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group ($-SO_3^-$ group) or a carboxylato group ($-COO^-$ group); m is 0 to 5; when there are a plurality of $R^5$s, they can be the same or different; each of $R^6$ and $R^7$ is independently a hydrogen atom, a halogen atom, or an alkyl group which can have a substituent group; and in $R^1$ to $R^5$, two sulfonato groups ($-SO_3^-$ groups) are contained, or one sulfonato group ($-SO_3^-$ group) and one carboxylato group ($-COO^-$ group) are contained.

2. The color material dispersion liquid according to claim 1, wherein the color material (A-1) is a color material which further contains a polyoxometalate anion and is represented by the following general formula (III):

General Formula (III)

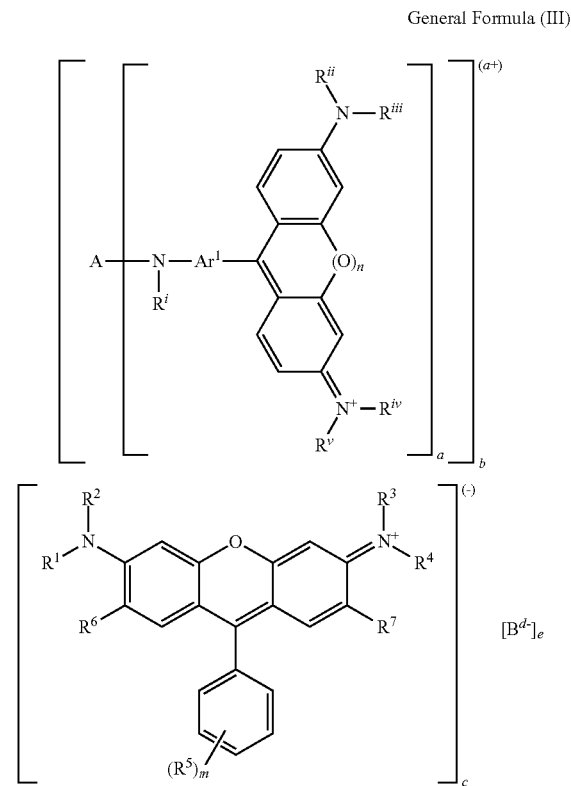

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$s can be the same or different; a plurality of $R^v$s can be the same or different; a plurality of $Ar^1$s can be the same or different; "a" is a number of 2 or more; b is a number of 1 or more; "n" is 0 or 1, and there is no bond when "n" is 0; a plurality of "n"s can be the same or different;

each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group (—$SO_3^-$ group) or a carboxylato group (—$COO^-$ group); m is 0 to 5; when there are a plurality of $R^5$s, they can be the same or different; each of $R^6$ and $R^7$ is independently a hydrogen atom, a halogen atom, or an alkyl group which can have a substituent group;

in $R^1$ to $R^5$ two sulfonato groups (—$SO_3^-$ groups) are contained, or one sulfonato group (—$SO_3^-$ group) and one carboxylato group (—$COO^-$ group) are contained; $B^{d-}$ is a "d"-valent polyoxometalate anion; and c and e are positive numbers.

3. The color material dispersion liquid according to claim 2, wherein the polyoxometalate anion in the color material represented by the general formula (III) contains at least tungsten, and a molar ratio of the tungsten to molybdenum in the polyoxometalate anion is 100:0 to 85:15.

4. A color resin composition for color filters, comprising: (A) a color material, (B) a dispersant, (C) a solvent and (D) a binder component, wherein the color material (A) contains a color material (A-1) in which at least a cation represented by the following general formula (I) and a monovalent anion represented by the following general formula (II) form a salt:

General Formula (I)

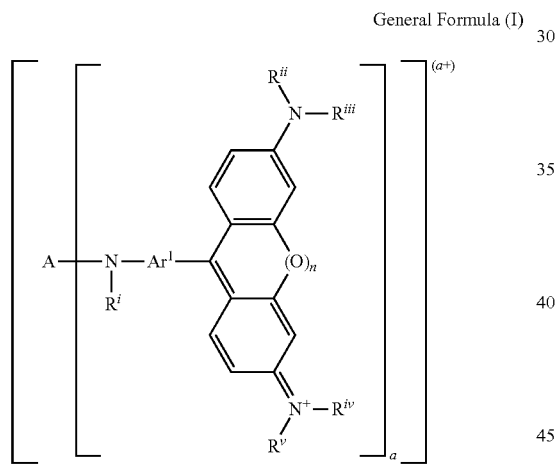

General Formula (II)

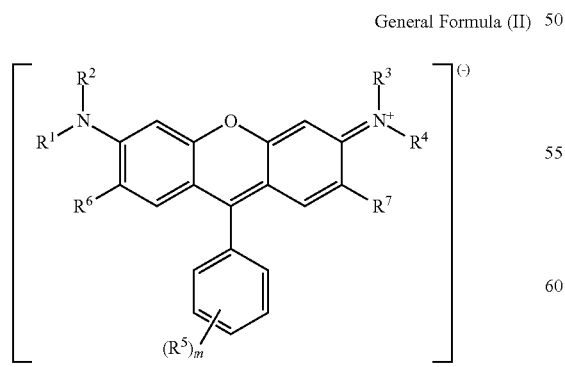

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$s can be the same or different; a plurality of $R^v$s can be the same or different; a plurality of $Ar^1$s can be the same or different;

"a" is a number of 2 or more; "n" is 0 or 1, and there is no bond when "n" is 0; and a plurality of "n"s can be the same or different; and wherein each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group (—$SO_3^-$ group) or a carboxylato group (—$COO^-$ group); m is 0 to 5; when there are a plurality of $R^5$s, they can be the same or different; each of $R^6$ and $R^7$ is independently a hydrogen atom, a halogen atom, or an alkyl group which can have a substituent group; and in $R^1$ to $R^5$, two sulfonato groups (—$SO_3^-$ groups) are contained, or one sulfonato group (—$SO_3^-$ group) and one carboxylato group (—$COO^-$ group) are contained.

5. The color resin composition for color filters according to claim 4, wherein the color material (A-1) is a color material which further contains a polyoxometalate anion and is represented by the following general formula (III):

General Formula (III)

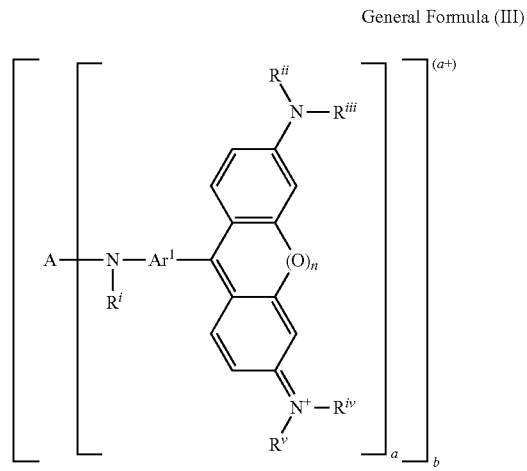

-continued

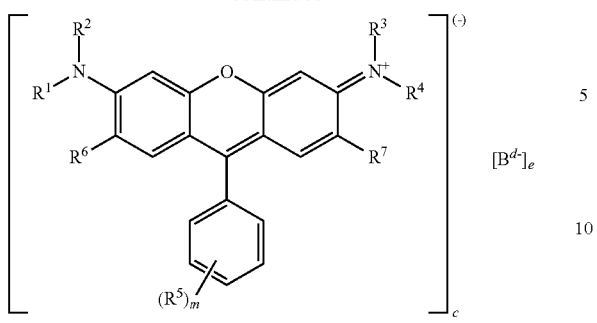

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$s can be the same or different; a plurality of $R^v$s can be the same or different; a plurality of $Ar^1$s can be the same or different;

"a" is a number of 2 or more; b is a number of 1 or more; "n" is 0 or 1, and there is no bond when "n" is 0; a plurality of "n"s can be the same or different;

each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group ($-SO_3^-$ group) or a carboxylato group ($-COO^-$ group); m is 0 to 5; when there are a plurality of $R^5$s, they can be the same or different; each of $R^6$ and $R^7$ is independently a hydrogen atom, a halogen atom, or an alkyl group which can have a substituent group;

in $R^1$ to $R^5$, two sulfonato groups ($-SO_3^-$ groups) are contained, or one sulfonato group ($-SO_3^-$ group) and one carboxylato group ($-COO^-$ group) are contained;

$B^{d-}$ is a "d"-valent polyoxometalate anion; and c and e are positive numbers.

6. The color resin composition for color filters according to claim 5, wherein the polyoxometalate anion in the color material represented by the general formula (III) contains at least tungsten, and a molar ratio of the tungsten to molybdenum in the polyoxometalate anion is 100:0 to 85:15.

7. A color filter comprising at least a transparent substrate and color layers disposed on the substrate, wherein at least one of the color layers contains a color material (A-1) in which at least a cation represented by the following general formula (I) and a monovalent anion represented by the following general formula (II) form a salt:

General Formula (I)

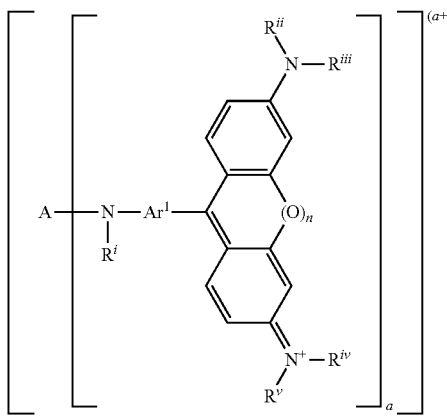

General Formula (II)

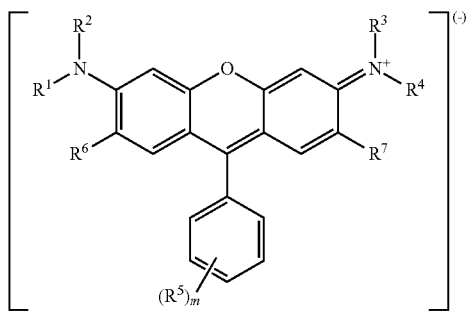

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$s can be the same or different; a plurality of $R^v$s can be the same or different; a plurality of $Ar^1$s can be the same or different;

"a" is a number of 2 or more; "n" is 0 or 1, and there is no bond when "n" is 0; and a plurality of "n"s can be the same or different; and wherein each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group ($-SO_3^-$ group) or a carboxylato group ($-COO^-$ group); m is 0 to 5; when there are a plurality of $R^5$s, they can be the same or different; each of $R^6$ and $R^7$ is independently a hydrogen atom, a halogen atom, or an alkyl group which can have a substituent group; and in $R^1$ to $R^5$, two sulfonato groups (—$SO_3^-$ groups) are contained, or one sulfonato group (—$SO_3^-$ group) and one carboxylato group (—$COO^-$ group) are contained.

8. A liquid crystal display device comprising the color filter defined by claim 7, a counter substrate, and a liquid crystal layer disposed between the color filter and the counter substrate.

9. An organic light-emitting display device comprising the color filter defined by claim 7 and an organic light-emitting material.

10. A color material represented by the following general formula (III'):

General Formula (III')

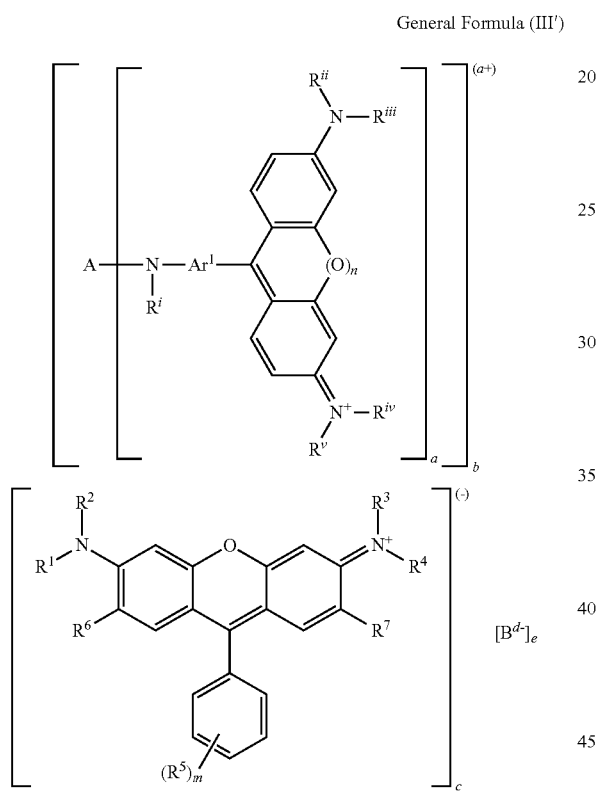

wherein A is an "a"-valent organic group in which a carbon atom directly bound to N has no π bond, and the organic group is an aliphatic hydrocarbon group having a saturated aliphatic hydrocarbon group at least at a terminal position directly bound to N, or an aromatic group having the aliphatic hydrocarbon group, and O, S, N can be contained in a carbon chain of the organic group; each of $R^i$ to $R^v$ is independently a hydrogen atom, an alkyl group which can have a substituent group, or an aryl group which can have a substituent group; $R^{ii}$ and $R^{iii}$ can be bound to form a ring structure, and/or $R^{iv}$ and $R^v$ can be bound to form a ring structure; $Ar^1$ is a divalent aromatic group which can have a substituent group; a plurality of $R^i$s can be the same or different; a plurality of $R^{ii}$s can be the same or different; a plurality of $R^{iii}$s can be the same or different; a plurality of $R^{iv}$s can be the same or different; a plurality of $R^v$s can be the same or different; a plurality of $Ar^1$s can be the same or different;

"a" is a number of 2 or more; b is a number of 1 or more; "n" is 0 or 1, and there is no bond when "n" is 0; a plurality of "n"s can be the same or different;

each of $R^1$ to $R^4$ is independently a hydrogen atom, an alkyl group which can have a substituent group, an aryl group which can have a substituent group, or an aralkyl group which can have a substituent group; $R^1$ and $R^2$ can be bound to form a ring structure, and/or $R^3$ and $R^4$ can be bound to form a ring structure; $R^5$ is a halogen atom, an alkyl group which can have a substituent group, a sulfonato group (—$SO_3^-$ group) or a carboxylato group (—$COO^-$ group); m is 0 to 5; when there are a plurality of $R^5$s, they can be the same or different; each of $R^6$ and $R^7$ is independently a hydrogen atom, a halogen atom, or an alkyl group which can have a substituent group;

in $R^1$ to $R^5$, two sulfonato groups (—$SO_3^-$ groups) are contained, or one sulfonato group (—$SO_3^-$ group) and one carboxylato group (—$COO^-$ group) are contained;

$B^{d-}$ is a "d"-valent polyoxometalate anion; c and e are positive numbers; and c:(d×e) is 5:95 to 50:50.

* * * * *